US009512414B2

(12) United States Patent
Okuma et al.

(10) Patent No.: US 9,512,414 B2
(45) Date of Patent: Dec. 6, 2016

(54) THERMOSTABLE BETA-GLUCOSIDASE

(71) Applicant: HONDA MOTOR CO., LTD., Minato-Ku, Tokyo (JP)

(72) Inventors: Jiro Okuma, Wako (JP); Migiwa Suda, Wako (JP); Asuka Yamaguchi, Wako (JE); Yoshitsugu Hirose, Wako (JP); Yasuhiro Kondo, Wako (JP); Masaru Sato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/964,216

(22) Filed: Dec. 9, 2015

(65) Prior Publication Data

US 2016/0168553 A1 Jun. 16, 2016

(30) Foreign Application Priority Data

Dec. 12, 2014 (JP) ................. 2014-252067

(51) Int. Cl.
| | |
|---|---|
| *C12N 9/42* | (2006.01) |
| *C12P 19/02* | (2006.01) |
| *C12N 9/38* | (2006.01) |
| *C12N 9/24* | (2006.01) |
| *C12P 19/14* | (2006.01) |

(52) U.S. Cl.
CPC ............. *C12N 9/2445* (2013.01); *C12N 9/248* (2013.01); *C12N 9/2471* (2013.01); *C12P 19/02* (2013.01); *C12P 19/14* (2013.01); *C12Y 302/01021* (2013.01); *C12Y 302/01023* (2013.01); *C12Y 302/01037* (2013.01)

(58) Field of Classification Search
CPC ....... C12N 9/2445; C12P 19/02; C12P 19/14
See application file for complete search history.

(56) References Cited

U.S. PATENT DOCUMENTS

| 2016/0032265 A1* | 2/2016 | Kondo | ............. | C12N 15/63 435/99 |
|---|---|---|---|---|
| 2016/0076015 A1* | 3/2016 | Hirose | ............. | C12N 9/2445 435/99 |
| 2016/0076016 A1* | 3/2016 | Hirose | ............. | C12N 9/2445 435/99 |
| 2016/0076017 A1* | 3/2016 | Kondo | ............. | C12N 9/2477 435/99 |

FOREIGN PATENT DOCUMENTS

| JP | 10-052274 A | 2/1998 |
|---|---|---|
| JP | 4689807 B2 | 2/2011 |
| JP | 2011-110011 A | 6/2011 |
| JP | 4801872 B2 | 10/2011 |

OTHER PUBLICATIONS

Jabbour et al. A novel thermostable and glucose-tolerant β-glucosidase from Fervidobacterium islandicum. Appl Microbiol Biotechnol. Mar. 2012;93(5):1947-56. doi: 10.1007/s00253-011-3406-0. Epub Dec. 8, 2011.*
Branden et al. Introduction to Protein Structure, Garland Publishing Inc., New York, p. 247, 1991.*
Parry et al., "Biochemical characterization and mechanism of action of a thermostable Beta-glucosidase purified from Thermoascus aurantiacus", Biochemical Journal, 2001, vol. 353, pp. 117-127.
Jabbour et al., "A novel thermostable and glucose-tolerant Beta-glucosidase from Fervidobacterium islandicum", Applied Microbiology and Biotechnology, 2012, vol. 93, pp. 1947-1956.
Saha et al., "Production, Purification, and Characterization of a Highly Glucose-Tolerant Novel Beta-Glucosidase from Candida peltata", Applied and Environmental Microbiology, 1996, vol. 62, pp. 3165-3170.
C. Riou et al., "Purification, Characterization, and Substrate Specificity of a Novel Highly Glucose-Tolerant Beta-Glucosidase from Aspergillus oryzae", Applied and Environmental Microbiology, 1998, vol. 64, pp. 3607-3614.
Quinlan et al., " Pyrobayes: an improved base caller for SNP discovery in pyrosequences", Nature Methods, 2008, vol. 5, pp. 179-181.
Hoff et al., "Orphelia: predicting genes in metagenomic sequencing reads", Nucleic Acids Research Database, 2009,37 (Web Server issue: W101-W105).
Finn et al., "The Pfam protein families database", Nucleic Acids Research, 2010, vol. 38, pp. D211-D222, Helsinki, Finland.
Durbin et al., 'The theory behind profile HMMs. Biological sequence analysis: probabilistic models of proteins and nucleic acids', 1998, Cambridge University Press.
Extended European Search Report issued in the corresponding EP patent application 15199316.9 with a mailing date of Apr. 20, 2016.
Database Protein (Online), beta-galactosidase(*Pseudothermotoga hypogea*), Aug. 5, 2014.
Jabbour et al., "A novel thermostable and glucose-tolerant Beta-glucosidase from Fervidobacterium islandicum", Applied Microbiology and Biotechnology, Springer, Berlin, DE, vol. 93, No. 5, Dec. 8, 2011, pp. 1947-1956.
Database Protein (Online), "beta-galactosidase(*Thermotoga caldifontis*)", Jan. 30, 2015.

* cited by examiner

*Primary Examiner* — Yong Pak
(74) *Attorney, Agent, or Firm* — Carrier Blackman & Associates, P.C.; Joseph P. Carrier; Fulchand P. Shende

(57) ABSTRACT

A thermostable β-glucosidase including a β-glucosidase catalytic domain, the β-glucosidase catalytic domain including:
(A) a polypeptide including an amino acid sequence represented by SEQ ID NO: 1 or 2;
(B) a polypeptide including an amino acid sequence in which at least one amino acid has been deleted, substituted, or added in the amino acid sequence represented by SEQ ID NO: 1 or 2, and having hydrolytic activity using p-nitrophenyl-β-D-glucopyranoside as a substrate at least under conditions of a temperature of 100° C. and a pH of 5.5; or
(C) a polypeptide including an amino acid sequence having at least 80% sequence identity with the amino acid sequence represented by SEQ ID NO: 1 or 2, and having hydrolytic activity using p-nitrophenyl-β-D-glucopyranoside as a substrate at least under conditions of a temperature of 100° C. and a pH of 5.5.

4 Claims, 5 Drawing Sheets

FIG. 1

```
AR19G-228    1   MFPKDFLFGASMSGFQVEMGVAKGDIDANTDWEVWVREPENIINAVVSGHLPEYGVGWYNF   62
T. thermarum 1   FPKDFLFGASMAGFQVEMGVGKGKDMDPNTDWFVWVREPENIFTGTVSGHLPEYGVGWYKLY  61

AR19G-228    63  PTIHKLASDEGMNVRTNIEWSRIEFPTIEDVKVETERTESGIVSVQIDERALKQLDELAAR  124
T. thermarum 62  ANLHDLAVDFEGMNCLRVMEWSRIEFKPTEDVPVHWS-ENGIREVKIDKTSLEKLDEIANK 122

AR19G-228    125 EAVEHYREIFSDVRKRGLKVFVNLIHFTLPIWLHDPTAVHRRQPIDKLGMASENIIVEFTKF 186
T. thermarum 123 SAVEHYREIFKDMKSRGLRLILNLAHFTLPIMLIDPWAVHRGIPTEKTGMVMEEKIVWEEAKF 184

AR19G-228    187 AAVVNMKFDDLIDMVSIFNEPNVVSQMGYVMSVSGEPPGIEDTEKFNSFVNQIVAHARAYD 248
T. thermarum 185 AAVLVDMVTIMNEPNVVSQMGYIMTRGGEPPSYFSPEMYLKSLENQAQAHARAYD     246

AR19G-228    249 AMKKLTDKPIGLIVYSASMVESTDGDAELEESVTHFMNFFEDALHSGTMFERTREDLAGRLD 310
T. thermarum 247 AIKFLTEKPVGIIVASSIVETLGDKEIEENAMYVMINYMFEDSIINGSLLFQDRPDWREKVD 308

AR19G-228    311 FIGLNVYIRTVIQRSLQELSEGPVSMSNSIVPGYGYAQPAGESKDGRPVSDFGWETYPEGI 372
T. thermarum 309 FLGVMYIRTIVJER-IEPWNWFGQIALNLKILEGYGYAGPPGGESKDFRPVSDFGWETYPEGL 369

AR19G-228    373 LKLLRAEDERVALPIVMENGVADARDMLRPVHLVAHLVAVEKAIEEGLNVKGYLHWSIVDN 434
T. thermarum 370 LKLLRAEFYERVKLPLVIENGVADCRDMLRPVHLVGHLYAVEKAIEDGIDVRGYLHWSIVDN 431

AR19G-228    435 VEWAKGYHMREGMAETNVQLKSYIPRPSWYIFREIVKNLSTEKFRSYLQSPYQIWKQNV* 493
T. thermarum 432 VEWARGYTMRFGLAEDVETKQLIPRPSWYIFREIVK                         468
```

THERMOSTABLE BETA-GLUCOSIDASE

TECHNICAL FIELD

The present invention relates to a thermostable β-glucosidase, a polynucleotide that encodes the aforementioned thermostable β-glucosidase, an expression vector for expressing the aforementioned thermostable β-glucosidase, a transformant incorporated with the aforementioned expression vector, and a method for producing a cellulose degradation product using the aforementioned thermostable β-glucosidase.

Priority is claimed on Japanese Patent Application No. 2014-252067, filed Dec. 12, 2014, the content of which is incorporated herein by reference.

BACKGROUND ART

Plant biomass or lignocellulose is the most abundant renewable energy source on earth. From the viewpoints of global environmental conservation and fossil fuel depletion, biorefinery using plant biomass as a biofuel or a raw material of chemical products such as ethanol has attracted attention. The main component in the dry weight of plant biomass is lignocellulose composed of polysaccharides, such as celluloses and hemicelluloses, and lignin. For example, polysaccharides are hydrolyzed into monosaccharides such as glucose and xylose by glycoside hydrolases, and are then used as a biofuel or a raw material of chemical products.

Lignocellulose having a complex structure is persistent and is difficult to degrade or hydrolyze with a single glycoside hydrolase enzyme. For the complete degradation of lignocellulose, in general, three types of enzymes, i.e., an endoglucanase (cellulase or endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21) are required. In addition, it is considered that an appropriate formulation of multiple enzymes is necessary, including a xylanase (endo-1,4-β-xylanase, EC 3.2.1.8) which is a hemicellulase and other plant cell wall degrading enzymes.

When cellulose is subjected to hydrolysis by cellobiohydrolase, cellobiose which is a disaccharide is mainly produced. β-glucosidase hydrolyzes this cellobiose into glucose, which is a monosaccharide, and is therefore one of the essential enzymes for degrading lignocellulose ultimately to monosaccharides.

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the biomass slurry (hydrolyzed biomass solution) is high, and the hydrolysis reaction of the lignocellulose tends to proceed poorly. Accordingly, by using a thermostable enzyme and performing the enzymatic hydrolysis treatment at a high temperature of 80° C. or higher, for example, the rate of the hydrolysis reaction can be increased, and the viscosity of the biomass slurry can be reduced, which is expected to enable a shortening of the hydrolysis reaction time and a reduction in the amount of enzyme required. As a result, for all of the various glycoside hydrolases, the development of enzymes having superior thermostability is very desirable.

Many thermostable enzymes have been obtained by cloning genes from thermophilic microorganisms that exist in high-temperature environments, determining the DNA sequence, and then expressing the DNA using *E. coli* or filamentous fungi or the like. For example, a thermostable β-glucosidase (with an optimum temperature of 70° C. and an optimum pH of 3.5 to 4.0) derived from a filamentous fungus *Acremonium cellulolyticus* has been disclosed in Patent Document 1. Three types of thermostable β-glucosidases (with an optimum temperature of 55° C. and an optimum pH of 4.5 to 5.1) derived from *Acremonium cellulolyticus* have been disclosed in Patent Document 2. A thermostable β-glucosidase (with an optimum temperature of 80° C. and an optimum pH of 5 to 6) derived from a *Thermoanaerobactor* species has been disclosed in Patent Document 3. A thermostable β-glucosidase (with an optimum temperature of 80° C. and an optimum pH of 4.6) derived from *Thermoascas auranticus* has been disclosed in Non-Patent Document 1. A thermostable β-glucosidase (with an optimum temperature of 90° C. and an optimum pH of 6 to 7) derived from *Fervidobacterium islandicum* has been disclosed in Non-Patent Document 2.

In addition, since β-glucosidases generally have characteristics so that their activities are inhibited by glucose which is their decomposition product, although the development of β-glucosidases that are less susceptible to glucose has been advanced, those having high thermostability are not available (for example, see Patent Document 4, and Non-Patent Documents 3 and 4).

PRIOR ART DOCUMENTS

Patent Documents

[Patent Document 1] Japanese Patent No. 4,801,872
[Patent Document 2] Japanese Patent No. 4,689,807
[Patent Document 3] Japanese Unexamined Patent Application, First Publication No. Hei 10-52274
[Patent Document 4] Japanese Unexamined Patent Application, First Publication No. 2011-110011

Non-Patent Documents

[Non-Patent Document 1] Neil et al., Biochemical Journal, 2001, vol. 353, p. 117-127.
[Non-Patent Document 2] Jabbour et al., Applied Microbiology and Biotechnology, 2012, vol. 93, p. 1947-1956.
[Non-Patent Document 3] Saha and Bothast, Applied and Environmental Microbiology, 1996, vol. 62, p. 3165-3170.
[Non-Patent Document 4] C. Riou et al., Applied and Environmental Microbiology, 1998, vol. 64, p. 3607-3614.

SUMMARY OF THE INVENTION

Problems to be Solved by the Invention

The present invention has an object of providing a novel thermostable β-glucosidase that exhibits hydrolytic activity using p-nitrophenyl-β-D-glucopyranoside (hereinafter, may be abbreviated as PNPG) as a substrate at least under conditions of a temperature of 100° C., and even under conditions where an extremely high concentration of glucose is present, a polynucleotide that encodes the aforementioned thermostable β-glucosidase, an expression vector for expressing the aforementioned thermostable β-glucosidase, a transformant incorporated with the aforementioned expression vector, and a method for producing a cellulose degradation product using the aforementioned thermostable β-glucosidase.

Means for Solving the Problem

In order to achieve the above object, the inventors of the present invention extracted DNA directly from the high-temperature soils of hot springs, and by carrying out a large-scale metagenomic sequencing of the microbial flora that was difficult to culture, they succeeded in obtaining a thermostable β-glucosidase having a novel amino acid sequence, thus enabling them to complete the present invention.

In other words, a thermostable β-glucosidase, a polynucleotide, an expression vector, a transformant, a method for producing the thermostable β-glucosidase, a glycoside hydrolase mixture, and a method for producing a cellulose degradation product according to the present invention include the aspects [1] to [12] described below.

[1] A thermostable β-glucosidase including a β-glucosidase catalytic domain, the β-glucosidase catalytic domain including:

(A) a polypeptide including an amino acid sequence represented by SEQ ID NO: 1 or 2;

(B) a polypeptide including an amino acid sequence in which at least one amino acid has been deleted, substituted, or added in the amino acid sequence represented by SEQ ID NO: 1 or 2, and having hydrolytic activity using p-nitrophenyl-β-D-glucopyranoside as a substrate at least under conditions of a temperature of 100° C. and a pH of 5.5; or (C) a polypeptide including an amino acid sequence having at least 80% sequence identity with the amino acid sequence represented by SEQ ID NO: 1 or 2, and having hydrolytic activity using p-nitrophenyl-β-D-glucopyranoside as a substrate at least under conditions of a temperature of 100° C. and a pH of 5.5.

[2] The thermostable β-glucosidase according to the aforementioned aspect [1], in which hydrolytic activity using p-nitrophenyl-β-D-glucopyranoside as a substrate in the presence of glucose where a glucose concentration becomes equal to or less than 1.2 M is at least 80% of the aforementioned hydrolytic activity in the absence of glucose.

[3] The thermostable β-glucosidase according to the aforementioned aspect [1] or [2], which also has β-galactosidase activity.

[4] The thermostable β-glucosidase according to any one of the aforementioned aspects [1] to [3], which also has β-xylosidase activity.

[5] A polynucleotide, having a region encoding a β-glucosidase catalytic domain, the region including:

(a) a nucleotide sequence encoding a polypeptide including the amino acid sequence represented by SEQ ID NO: 1 or 2;

(b) a nucleotide sequence encoding a polypeptide which includes an amino acid sequence in which at least one amino acid has been deleted, substituted, or added in the amino acid sequence represented by SEQ ID NO: 1 or 2, and has hydrolytic activity using p-nitrophenyl-β-D-glucopyranoside as a substrate at least under conditions of a temperature of 100° C. and a pH of 5.5;

(c) a nucleotide sequence encoding a polypeptide which includes an amino acid sequence having at least 80% sequence identity with the amino acid sequence represented by SEQ ID NO: 1 or 2, and has hydrolytic activity using p-nitrophenyl-β-D-glucopyranoside as a substrate at least under conditions of a temperature of 100° C. and a pH of 5.5;

(d) a nucleotide sequence, having at least 80% sequence identity with a nucleotide sequence represented by SEQ ID NO: 3 or 4, and encoding a polypeptide that has hydrolytic activity using p-nitrophenyl-β-D-glucopyranoside as a substrate at least under conditions of a temperature of 100° C. and a pH of 5.5; or (e) a nucleotide sequence of a polynucleotide which hybridizes with a polynucleotide including the nucleotide sequence represented by SEQ ID NO: 3 or 4 under a stringent condition, the nucleotide sequence encoding a polypeptide having hydrolytic activity using p-nitrophenyl-β-D-glucopyranoside as a substrate at least under conditions of a temperature of 100° C. and a pH of 5.5.

[6] The polynucleotide according to the aforementioned aspect [5], in which hydrolytic activity of the aforementioned polypeptide using p-nitrophenyl-β-D-glucopyranoside as a substrate in the presence of glucose where a glucose concentration becomes equal to or less than 1.2 M is equal to or more than 80% of the aforementioned hydrolytic activity in the absence of glucose.

[7] The polynucleotide according to the aforementioned aspect [5] or [6], in which the aforementioned polypeptide also has β-galactosidase activity.

[8] The polynucleotide according to any one of the aforementioned aspects [5] to [7], in which the aforementioned polypeptide also has β-xylosidase activity.

[9] An expression vector incorporating the polynucleotide according to any one of the aforementioned aspects [5] to [8], the expression vector being capable of expressing a polypeptide having β-glucosidase activity in a host cell.

[10] A transformant into which the expression vector according to the aforementioned aspect [9] has been introduced.

[11] The transformant according to the aforementioned aspect [9], which is a eukaryotic microbe.

[12] A method for producing a thermostable β-glucosidase, the method including a step of generating a thermostable β-glucosidase in the transformant according to the aforementioned aspect [9] or [10].

[13] A glycoside hydrolase mixture, including the thermostable β-glucosidase according to any one of the aforementioned aspects [1] to [4], a thermostable β-glucosidase encoded by the polynucleotide according to any one of the aforementioned aspects [5] to [8], or a thermostable β-glucosidase produced by the method for producing a thermostable β-glucosidase according to the aforementioned aspect [12], and at least one other glycoside hydrolase.

[14] A method for producing a lignocellulose degradation product, the method including a step of producing a lignocellulose degradation product by bringing a material composed of lignocellulose containing cellulose into contact with the thermostable β-glucosidase according to any one of the aforementioned aspects [1] to [4], a thermostable β-glucosidase encoded by the polynucleotide according to any one of the aforementioned aspects [5] to [8], the transformant according to the aforementioned aspect [10] or [11], a thermostable β-glucosidase produced by the method for producing a thermostable β-glucosidase according to the aforementioned aspect [12], or the glycoside hydrolase mixture according to the aforementioned aspect [13].

Effects of the Invention

The thermostable β-glucosidase according to the present invention has hydrolytic activity using PNPG as a substrate at least under conditions of a temperature of 100° C. and a pH of 5.5. For this reason, the aforementioned thermostable β-glucosidase is suitable for a hydrolysis process of materials composed of lignocellulose containing cellulose, for example, materials containing a compound having β-glycosidic bonds, under high temperature conditions.

Further, in another aspect, aforementioned thermostable β-glucosidase is suitable for a hydrolysis process of materials containing galactose residues, under high temperature conditions. In addition, the polynucleotide, the expression vector incorporated with the aforementioned polynucleotide and the transformant introduced with the aforementioned expression vector according to the present invention are suitably used for the production of the thermostable β-glucosidase according to the present invention.

BRIEF DESCRIPTION OF THE DRAWINGS

FIG. 1 is an alignment diagram of the amino acid sequence (SEQ ID NO: 1) encoded by the open reading frame AR19G-228, and the amino acid sequence (SEQ ID NO: 8) of the glycoside hydrolase family 1 of *Thermotoga thermarum* DSM 5069 of the phylum Thermotogae.

DETAILED DESCRIPTION OF THE INVENTION

Thermostable β-glucosidase

Figure 2:
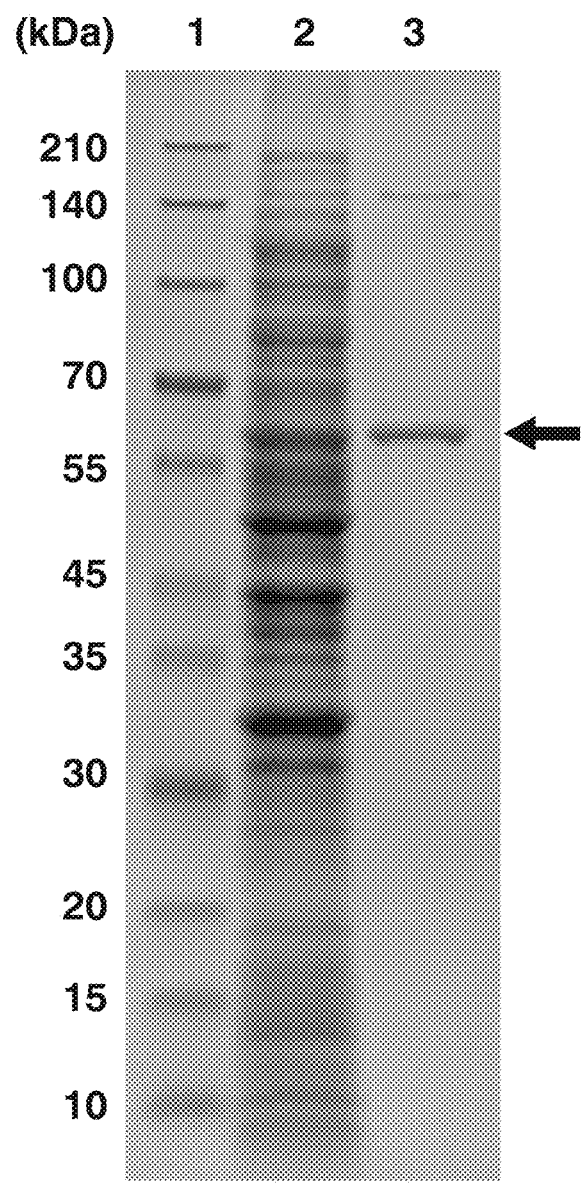
FIG. 2 is a diagram showing the SDS-PAGE analysis result of the AR19G-228-1 protein obtained by expressing the AR19G-228-1 gene in *E. coli* in Example 1.

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that only a mere 0.1% or less of the microorganisms that exist in soils have been able to be isolated and cultured with currently available microbial culturing techniques. This difficulty in culturing microorganisms from high-temperature soils is one of the reasons hindering the development of thermostable enzymes.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture.

As shown in Example 1 described below, the inventors of the present invention extracted the genomic DNA (metagenomic DNA) of microbial groups from collected high-temperature hot spring soils (for example, hot spring water of 58 to 78° C. containing soil, mud, biomat and biofilm and the like), and conducted shotgun sequencing and annotation of the metagenomic DNA, thus obtaining open reading frames (ORFs) encoding amino acid sequences similar to known β-glucosidase enzymes (for example, amino acid sequences having 20% or higher sequence identity, and an expectation value (E-value) of less than $1e^{-20}$). For each of the obtained ORFs for which a β-glucosidase catalytic domain was confirmed, a primer was designed based on the nucleotide sequence information of the ORF, and gene candidates were cloned from the metagenomic DNA of the high-temperature hot spring soils by the PCR method. The PCR-cloned DNAs were incorporated into *E. coli*, and proteins encoded by these nucleotide sequences were expressed, and subjected to functional screening by PNPG degradation activity assay. Finally, a thermostable β-glucosidase (hereafter also referred to as "AR19G-228-1") having PNPG degradation activity was obtained from these ORFs. The amino acid sequence of AR19G-228-1 and the nucleotide sequence encoding the amino acid sequence of AR19G-228-1 are represented by SEQ ID NO: 2 and SEQ ID NO: 4, respectively.

As shown in Example 1 described below, AR19G-228-1 exhibits the highest hydrolytic activity against PNPG, also exhibits high hydrolytic activity against p-nitrophenyl-β-D-galactopyranoside (hereinafter, may be abbreviated as PNP-GAL), and also exhibits a little bit of degradation activity against p-nitrophenyl-β-D-xylopyranoside (hereinafter, may be abbreviated as PNPX), phosphoric acid swollen Avicel (hereinafter, may be abbreviated as PSA), the crystalline cellulose Avicel (Avicel), xylan, and carboxymethyl cellulose (CMC). From this substrate specificity, AR19G-228-1 is suggested to be a glycoside hydrolase having β-glucosidase activity and β-galactosidase activity which also has a little bit of β-xylosidase activity.

It should be noted that in the present description, the expression "β-glucosidase activity" means an activity that produces a monosaccharide, when a compound containing a β-glycosidic bond is used as a substrate, by hydrolyzing the substrate.

The "compound containing a β-glycosidic bond" can be exemplified by, for example, a glucan having a β-glycosidic bond, an oligosaccharide having a β-glycosidic bond, and the like. In addition, in the present description, the expression "β-xylosidase activity" means an enzymatic activity that promotes the hydrolysis of materials containing a compound or oligosaccharide having a β-xylosidic bond, and its activity value is represented by the hydrolytic activity using PNPX as a substrate.

Further, in the present description, the expression "β-galactosidase activity" means an activity to hydrolyze the β-glucosidic bonds between galactoses or between a galactose and another monosaccharide.

Furthermore, in the present description, the expression "has activity" or "exhibits activity" means that the enzyme acts against at least one substrate, with a significant difference occurring in the amount of reducing ends or the color development reaction of the hydrolyzed substrate compared with a negative control.

Accordingly, the expression "has β-glucosidase activity" means that the enzyme acts at least against a compound containing a β-glycosidic bond as a substrate, and generates a significant difference in the amount of reducing ends or the color development reaction of the hydrolyzed substrate compared with a negative control.

Further, in yet another aspect, the expression "has β-glucosidase activity" means that the enzyme acts at least against PNPG as a substrate, and generates a significant difference in the amount of reducing ends or the color development reaction of the hydrolyzed substrate compared with a negative control.

The expression "has β-xylosidase activity" means that the enzyme acts at least against PNPX as a substrate, and generates a significant difference in the amount of reducing ends or the color development reaction of the hydrolyzed substrate compared with a negative control.

The expression "has β-galactosidase activity" means that the enzyme acts at least against a compound in which galactoses are mutually bonded or a compound in which a galactose and another monosaccharide are bonded by a β-glucosidic bond as a substrate, and generates a significant difference in the amount of reducing ends or the color development reaction of the hydrolyzed substrate compared with a negative control.

In addition, when the amino acid sequence of AR19G-228-1 was searched against a database of known amino acid sequences, the amino acid sequence that showed the highest sequence identity was that of the glycoside hydrolase family 1 (Genbank accession ID: AEH51094.1) (SEQ ID NO: 8) of *Thermotoga thermarum* DSM 5069, and the sequence identity (homology) was 68% for the GH1 catalytic domain. From the substrate specificity and the sequence identity of the amino acid sequence with that of a known protein, it became clear that AR19G-228-1 is a novel β-glucosidase belonging to the GH family 1.

AR19G-228-1 has hydrolytic activity using PNPG as a substrate at least under conditions of a temperature of 100° C. and a pH of 5.5. Actually, as shown in Example 1 described below, AR19G-228-1 exhibits β-glucosidase activity within a temperature range from 50 to 110° C., and exhibits particularly strong β-glucosidase activity in a temperature range from 90 to 105° C. More specifically, the β-glucosidase activity of AR19G-228-1 tended to increase with increasing temperature within a range from 50 to 100° C., and decrease rapidly above 105° C.

Generally, in a protein having some form of bioactivity, one or a plurality of amino acids can be deleted, substituted, or added, without impairing the bioactivity. In other words, in AR19G-228-1, one or a plurality of amino acids can be deleted, substituted, or added without impairing the glycoside hydrolysis activity including the β-glucosidase activity.

Hence, the thermostable β-glucosidase according to the present invention is a thermostable β-glucosidase having a β-glucosidase catalytic domain which includes any one of the following (A) to (C):

(A) a polypeptide including an amino acid sequence represented by SEQ ID NO: 1 or 2 (namely, an open reading frame AR19G-228 or a gene clone AR19G-228-1);

(B) a polypeptide including an amino acid sequence in which at least one amino acid has been deleted, substituted, or added in the amino acid sequence represented by SEQ ID NO: 1 or 2, and having hydrolytic activity using PNPG as a substrate at least under conditions of a temperature of 100° C. and a pH of 5.5; or (C) a polypeptide including an amino acid sequence having at least 80% sequence identity with the amino acid sequence represented by SEQ ID NO: 1 or 2, and having hydrolytic activity using PNPG as a substrate at least under conditions of a temperature of 100° C. and a pH of 5.5.

It should be noted that the amino acid sequence represented by SEQ ID NO: 1 is an amino acid sequence encoded by the open reading frame "AR19G-228" (SEQ ID NO: 3) belonging to the GH family 1 which is estimated to be a candidate sequence of β-glucosidase by the analysis using a database from the hot spring soil sample, by the method described in Example 1 to be mentioned later.

In the present description, a "polypeptide in which an amino acid is deleted" means a polypeptide in which a portion of the amino acids which constitute the polypeptide is missing (removed).

In the present description, a "polypeptide in which an amino acid is substituted" means a polypeptide in which an amino acid which constitutes the polypeptide has been replaced with a different amino acid.

In the present description, a "polypeptide in which an amino acid is added" means a polypeptide in which a new amino acid has been inserted within the polypeptide.

In the aforementioned polypeptide of (B), the number of amino acids deleted, substituted, or added in the amino acid sequence represented by SEQ ID NO: 1 or 2 is preferably 1 to 20, more preferably 1 to 10, and still more preferably 1 to 5.

In the aforementioned polypeptide of (C), the sequence identity with the amino acid sequence represented by SEQ ID NO: 1 or 2 is not specifically limited as long as it is 80% or greater but less than 100%, but the sequence identity is preferably 85% or greater but less than 100%, more preferably 90% or greater but less than 100%, still more preferably 95% or greater but less than 100%, and most preferably 98% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity value between amino acid sequences in the present invention is obtained by calculation on the basis of an alignment obtained from the publicly known homology search software BLASTP.

The aforementioned polypeptides of (B) and (C) may be artificially designed, or may be homologues of AR19G-228-1 or the like, or partial proteins thereof.

Each of the aforementioned polypeptides of (A) to (C) may be chemically synthesized based on the amino acid sequence, or may be generated by a protein expression system using the polynucleotide according to the present invention described below. Further, each of the polypeptides of (B) and (C) can also be artificially synthesized based on the polypeptide including the amino acid sequence represented by SEQ ID NO: 1 or 2, by using a gene recombination technique to introduce amino acid mutation(s).

Each of the polypeptides of (A) to (C) has hydrolytic activity (β-glucosidase activity) using PNPG as a substrate at least under conditions of a temperature of 100° C. and a pH of 5.5. As a result, a thermostable β-glucosidase can be obtained by having any of the polypeptides of (A) to (C) as the β-glucosidase catalytic domain.

The thermostable β-glucosidase according to the present invention uses PNPG as a substrate. In addition to PNPG, the thermostable β-glucosidase may also use another β-glucan, oligosaccharide, or the like than PNPG, as a substrate. Examples of substrates that can act as substrates for the thermostable β-glucosidase according to the present invention include PNPGAL; PNPX; xylan; crystalline celluloses such as Avicel, crystalline bacterial cellulose (bacterial microcrystalline cellulose, BMCC) and filter paper; PSA; CMC; glucans composed of β-1,4 linkages; oligosaccharides composed of β-1,4 linkages such as cellobiose; glucans composed of β-1,3 and β-1,4 linkages such as lichenan; glucans composed of β-1,3 and β-1,6 linkages such as laminarin; glucans composed of β-1,3 linkages; glucans composed of β-1,6 linkages; and oligosaccharides composed of β-1,6 linkages such as gentiobiose. The thermostable β-glucosidase according to the present invention preferably also uses PNPGAL as a substrate, in addition to PNPG, and more preferably also uses at least one member selected from the group consisting of PNPX, PSA, Avicel, xylan, and CMC as a substrate, in addition to PNPG and PNPGAL.

The thermostable β-glucosidase according to the present invention exhibits hydrolytic activity (β-glucosidase activity) using PNPG as a substrate at least under conditions of a pH of 5.5, and preferably within a temperature range from 80 to 105° C., more preferably within a temperature range from 70 to 105° C., and still more preferably within a temperature range from 50 to 105° C. The optimum temperature of the thermostable β-glucosidase according to the present invention is preferably within a range from 80 to 110° C., more preferably within the range from 90 to 105° C., and still more preferably within the range from 95 to 105° C.

It should be noted that the expression "thermostable" with respect to the thermostable β-glucosidase according to the present invention refers to a β-glucosidase activity within the temperature range from 50 to 110° C.

The optimum pH of the thermostable β-glucosidase according to the present invention is within a range from pH 5.0 to 6.5. The thermostable β-glucosidase according to the present invention preferably exhibits β-glucosidase activity at least within a range from pH 5.0 to 7.0, and more preferably exhibits β-glucosidase activity within a range of pH 4.5 to 7.0.

The thermostable β-glucosidase according to the present invention is preferably less susceptible to influence (inhibition) even in the presence of high concentrations of glucose. For the thermostable β-glucosidase according to the present invention, the hydrolytic activity using PNPG as a substrate in the presence of glucose where the glucose concentration becomes equal to or less than 1.2 M is preferably equal to or more than 80% of the hydrolytic activity in the absence of glucose, and the hydrolytic activity using PNPG as a substrate in the presence of glucose where the glucose concentration becomes equal to or less than 1.2 M is more preferably equal to or more than 85% of the hydrolytic activity in the absence of glucose. Further, in a separate aspect, the hydrolytic activity using PNPG as a substrate in the presence of glucose where the glucose concentration becomes equal to or less than 1.8 M is also preferably equal to or more than 60% of the hydrolytic activity in the absence of glucose.

The thermostable β-glucosidase according to the present invention may also have, in addition to the β-glucosidase activity, another type of cellulose hydrolysis activity other than the β-glucosidase activity. Examples of this another type of cellulose hydrolysis activity include β-galactosidase activity, xylanase activity, endoglucanase activity, xylosidase activity, or cellobiohydrolase activity. The thermostable β-glucosidase according to the present invention preferably also has β-galactosidase activity in addition to the β-glucosidase activity, and more preferably also has β-galactosidase activity and β-xylosidase activity in addition to the β-glucosidase activity.

The thermostable β-glucosidase according to the present invention may be an enzyme composed solely of the β-glucosidase catalytic domain including any of the aforementioned polypeptides of (A) to (C), or may be an enzyme further including other domains. Examples of these other domains include a domain of conventionally known β-glucosidases other than the β-glucosidase catalytic domain. For example, the thermostable β-glucosidase according to the present invention also includes enzymes obtained by substituting a β-glucosidase catalytic domain in a publicly known β-glucosidase with any of the aforementioned polypeptides of (A) to (C).

If the thermostable β-glucosidase according to the present invention includes a domain other than the β-glucosidase catalytic domain, it is preferable to include a cellulose-binding module. The cellulose-binding module may be either on the upstream (N-terminal side) or the downstream (C-terminal side) of the β-glucosidase catalytic domain. In addition, the cellulose-binding module and the β-glucosidase catalytic domain may be directly linked, or linked via a linker domain of an appropriate length. The thermostable β-glucosidase according to the present invention is preferably such that the cellulose-binding module is present on the upstream or the downstream of the β-glucosidase catalytic domain via a linker domain, more preferably such that the cellulose-binding module is present on the upstream of the β-glucosidase catalytic domain via a linker domain.

The cellulose-binding module contained in the thermostable β-glucosidase according to the present invention may suffice if it is a domain having an ability to bind to cellulose, for example, a domain having an ability to bind to PSA or a crystalline Avicel. The amino acid sequence thereof is not particularly limited. As the cellulose-binding module, for example, a cellulose-binding module of an already known protein or appropriately modified product thereof may be used. In addition, if the thermostable β-glucosidase according to the present invention has a β-glucosidase catalytic domain and a cellulose-binding module, it is preferable that these are linked via a linker sequence. The amino acid sequence, the length, and the like, of the linker sequence are not particularly limited.

The thermostable β-glucosidase according to the present invention may also have, at either the N-terminal or the C-terminal, a signal peptide capable of migration to and localization within a specific region within a cell, or a signal peptide that causes secretion from a cell. Examples of these signal peptides include an apoplastic transport signal peptide, an endoplasmic reticulum retention signal peptide, a nuclear transport signal peptide, or a secretory signal peptide. Specific examples of the endoplasmic reticulum retention signal peptide include signal peptides including an HDEL amino acid sequence. In those cases where the thermostable β-glucosidase according to the present invention has a signal peptide at the N-terminal or the C-terminal, the thermostable β-glucosidase expressed in a transformant can be secreted from the cell or localized within the endoplasmic reticulum or the like of the cells.

In addition, the thermostable β-glucosidase according to the present invention may also have various types of tags added, for example at the N-terminal or the C-terminal of the thermostable β-glucosidase, so as to facilitate easy purification in the case of generation using an expression system. Examples of tags that may be used include the types of tags widely used in the expression or purification of recombinant proteins, such as a His tag, an HA (hemagglutinin) tag, a Myc tag and a Flag tag.

In other words, one aspect of the thermostable β-glucosidase according to the present invention includes: the β-glucosidase catalytic domain including any of the aforementioned polypeptides of (A) to (C); and at least one member selected from the group consisting of a cellulose-binding module located either on the upstream (N-terminal side) or the downstream (C-terminal side) of the aforementioned β-glucosidase catalytic domain, a linker domain, a signal peptide added at either the N-terminal or the C-terminal of the aforementioned thermostable β-glucosidase, and a tag added at either the N-terminal or the C-terminal of the aforementioned thermostable β-glucosidase.

[Polynucleotide Encoding Thermostable β-Glucosidase]

The polynucleotide according to the present invention encodes the thermostable β-glucosidase according to the present invention. The aforementioned thermostable β-glucosidase can be generated by using the expression system of a host made by introducing an expression vector incorporated with the polynucleotide into the host.

More specifically, the polynucleotide according to the present invention is a polynucleotide having a region that encodes a β-glucosidase catalytic domain, the region including any one of the following nucleotide sequences (a) to (e):

(a) a nucleotide sequence encoding a polypeptide including the amino acid sequence represented by SEQ ID NO: 1 or 2;

(b) a nucleotide sequence encoding a polypeptide which includes an amino acid sequence in which at least one amino acid has been deleted, substituted, or added in the amino acid sequence represented by SEQ ID NO: 1 or 2, and has hydrolytic activity using PNPG as a substrate at least under conditions of a temperature of 100° C. and a pH of 5.5;

(c) a nucleotide sequence encoding a polypeptide which includes an amino acid sequence having at least 80% sequence identity with the amino acid sequence represented by SEQ ID NO: 1 or 2, and has hydrolytic activity using PNPG as a substrate at least under conditions of a temperature of 100° C. and a pH of 5.5;

(d) a nucleotide sequence, having at least 80% sequence identity with a nucleotide sequence represented by SEQ ID NO: 3 or 4, and encoding a polypeptide that has hydrolytic activity using PNPG as a substrate at least under conditions of a temperature of 100° C. and a pH of 5.5; or (e) a nucleotide sequence of a polynucleotide which hybridizes with a polynucleotide including the nucleotide sequence represented by SEQ ID NO: 3 or 4 under a stringent condition, the nucleotide sequence encoding a polypeptide having hydrolytic activity using PNPG as a substrate at least under conditions of a temperature of 100° C. and a pH of 5.5.

In the present description, a "polynucleotide in which a nucleotide is deleted" means a polynucleotide in which a portion of the nucleotides which constitute the polynucleotide is missing (removed).

In the present description, a "polynucleotide in which a nucleotide is substituted" means a polynucleotide in which a nucleotide which constitutes the polynucleotide has been replaced with a different nucleotide.

In the present description, a "polynucleotide in which a nucleotide is added" means a polynucleotide in which a new nucleotide has been inserted within the polynucleotide.

In the present invention and the description of this application, the expression "stringent condition" can be exemplified by the method described in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing performed after the incubation is preferably 1×SSC solution containing 0.1% by mass of SDS, and is more preferably 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be the nucleotide sequence represented by SEQ ID NO: 3, the nucleotide sequence represented by SEQ ID NO: 4, or a nucleotide sequence obtained by modifying the nucleotide sequence represented by SEQ ID NO: 3 or 4 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 3 or 4 may be chemically synthesized based on the nucleotide sequence information, or may be obtained from the natural world by using gene recombination techniques as either a full length gene that encodes AR19G-228-1 (hereinafter, may be referred to as the "AR19G-228-1 gene") or a partial region thereof including the β-glucosidase catalytic domain. The full length of the AR19G-228-1 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 3 or 4. The cDNA synthesized by a reverse transcription reaction using mRNA recovered from the sample as a template may also be used as a template. The sample from which the nucleic acid for use as a template is recovered is preferably a sample collected from a high-temperature environment such as hot spring soil.

In the aforementioned nucleotide sequence of (d), the sequence identity with the nucleotide sequence represented by SEQ ID NO: 3 or 4 is not specifically limited as long as it is 80% or greater but less than 100%, but the sequence identity is preferably 85% or greater but less than 100%, more preferably 90% or greater but less than 100%, and still more preferably 95% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity value between nucleotide sequences in the present invention is obtained by calculation on the basis of an alignment obtained from the publicly known homology search software BLASTN.

For example, each of the polynucleotides including the aforementioned nucleotide sequence of (b), (c) or (d) can be artificially synthesized by deleting, substituting, or adding one or a plurality of nucleotides in a polynucleotide including the nucleotide sequence represented by SEQ ID NO: 3 or 4. Further, the nucleotide sequence of (b), (c) or (d) may also be a full length sequence of a homologous gene of the AR19G-228-1 gene or a partial sequence thereof. The homologous gene of the AR19G-228-1 gene can be obtained by a gene recombination technique used in obtaining homologous genes of a gene for which the nucleotide sequence is already known.

The polynucleotide according to the present invention may have only the region encoding the β-glucosidase catalytic domain, or may also have, in addition to this region, one or more other regions encoding a cellulose-binding module, a linker sequence, various types of signal peptides, or various types of tags or the like.

In other words, one aspect of the polynucleotide according to the present invention includes: a region encoding a β-glucosidase catalytic domain, the region including any one of the aforementioned nucleotide sequences of (a) to (e); and a region encoding at least one member selected from the group consisting of a cellulose-binding module, a linker sequence, a signal peptide, and a tag.

[Expression Vector]

The expression vector according to the present invention incorporates the aforementioned polynucleotide according to the present invention, and is capable of expressing, in a host cell, a polypeptide (β-glucosidase) having hydrolytic activity using PNPG as a substrate at least under conditions of a temperature of 100° C. and a pH of 5.5. In other words, the expression vector of the present invention is an expression vector into which the polynucleotide according to the present invention has been incorporated in a state capable of expressing the thermostable β-glucosidase according to the present invention. More specifically, it is necessary that an expression cassette, composed, in order from the upstream side, of DNA having a promoter sequence, the aforementioned polynucleotide according to the present invention and DNA having a terminator sequence, is incorporated into the expression vector. Incorporation of the polynucleotide into an expression vector can be achieved using known gene recombination techniques. A commercially available expression vector preparation kit may also be used to achieve incorporation of the polynucleotide into the expression vector.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as *E. coli*, or a vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of host cells transformed by the expression vector and non-transformed host cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the aforementioned thermostable β-glucosidase according to the present invention can be expressed. The host into which the expression vector is introduced may be a prokaryotic cell such as *E. coli*, or a eukaryotic cell such as a yeast, a filamentous fungus, an insect cultured cell, a mammalian cultured cell, or a plant cell. In other words, examples of the transformant according to the present invention include *E. coli*, a yeast, a filamentous fungus, an insect cultured cell, a mammalian cultured cell or a plant cell into which the expression vector according to the present invention has been introduced. By culturing a transformant of *E. coli*, the thermostable β-glucosidase according to the present invention can be generated more easily and in large amounts. On the other hand, because proteins are glycosylated in eukaryotic cells, by using a transformant of a eukaryotic cell, a thermostable β-glucosidase can be generated which exhibits superior thermostability to that achieved by using a transformant of a prokaryotic cell.

There are no particular limitations on the method used for producing the transformant using the expression vector, and the types of methods typically used in the production of transformants can be employed. Examples of methods that can be used include an *Agrobacterium*-mediated method, a particle gun method, an electroporation method, and a PEG (polyethylene glycol) method. Of these, if the host is a plant cell, a particle gun method or an *Agrobacterium*-mediated method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable β-Glucosidase]

The method for producing a thermostable β-glucosidase according to the present invention is a method for generating a thermostable β-glucosidase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable β-glucosidase according to the present invention can be expressed constitutively within the transformant. On the other hand, in the case of a transformant produced using a so-called expression inducible promoter to induce the expression by means of a specific compound or temperature condition or the like, the thermostable β-glucosidase according to the present invention can be expressed in the transformant by conducting an induction treatment suitable for the respective expression-inducing condition.

The thermostable β-glucosidase generated by the transformant may be used in a state where it is retained inside the transformant, or may be extracted from the transformant and purified.

The method used for extracting and purifying the thermostable β-glucosidase from the transformant is not particularly limited, as long as the method does not impair the activity of the thermostable β-glucosidase, and extraction can be carried out by methods commonly used for extracting polypeptides from cells or biological tissue. Examples of the method include a method in which the transformant is immersed in an appropriate extraction buffer to extract the thermostable β-glucosidase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable β-glucosidase in the liquid extract can be purified by known purification methods such as a salting-out method, ultrafiltration method, or chromatography method.

If the thermostable β-glucosidase according to the present invention is expressed in a state having a secretory signal peptide in the transformant, then a solution containing the thermostable β-glucosidase can be readily obtained by culturing the transformant and then collecting the culture liquid supernatant obtained by removal of the transformant from the obtained culture. Further, if the thermostable β-glucosidase according to the present invention has a tag such as a His tag, then the thermostable β-glucosidase in the liquid extract or in the culture supernatant can be easily purified by an affinity chromatography method using the tag.

In other words, the method for producing a thermostable β-glucosidase according to the present invention includes generating the thermostable β-glucosidase within the transformant according to the present invention, and, according to need, extracting the thermostable β-glucosidase from the transformant and purifying the thermostable β-glucosidase.

[Glycoside Hydrolase Mixture]

The glycoside hydrolase mixture according to the present invention is a mixture containing the aforementioned thermostable β-glucosidase according to the present invention or a thermostable β-glucosidase produced by the aforementioned method for producing a thermostable β-glucosidase according to the present invention, and at least one other glycoside hydrolase. The thermostable β-glucosidase produced by the aforementioned method for producing a thermostable β-glucosidase according to the present invention may be in a state where it is retained inside the transformant, or may be extracted from the transformant and purified. By using the thermostable β-glucosidase according to the present invention as a mixture with one or more other glycoside hydrolases in a reaction to degrade a lignocellulose-containing material containing cellulose, the material composed of lignocellulose containing persistent cellulose can be degraded more efficiently.

There are no particular limitations on the other glycoside hydrolase besides the aforementioned thermostable β-glucosidase included in the glycoside hydrolase mixture, as long as it exhibits hydrolysis activity against cellulose or hemicellulose. Examples of the other glycoside hydrolase besides the aforementioned β-glucosidase included in the glycoside hydrolase mixture include xylanases, or hemicellulases such as β-xylosidases, as well as cellobiohydrolases, β-glucosidases and endoglucanases. The glycoside hydrolase mixture according to the present invention is preferably a mixture containing at least one of a hemicellulase and an endoglucanase in addition to the aforementioned thermostable β-glucosidase, and is more preferably a mixture containing both a hemicellulase and an endoglucanase in addition to the aforementioned thermostable β-glucosidase. Among the various possibilities, a mixture further containing at least one or more glycoside hydrolases selected from the group consisting of xylanases, β-xylosidases, cellobiohydrolases, and endoglucanases in addition to the aforementioned thermostable β-glucosidase is preferred; and a mixture further containing all of a xylanase, a β-xylosidase, a cellobiohydrolase and an endoglucanase in addition to the aforementioned thermostable β-glucosidase is more preferred.

The other glycoside hydrolase included in the glycoside hydrolase mixture is preferably a thermostable glycoside hydrolase having glycoside hydrolytic activity at least at 85° C., and is more preferably a thermostable glycoside hydrolase having glycoside hydrolytic activity at 70 to 90° C. By ensuring that all of the enzymes contained in the glycoside hydrolase mixture are thermostable (that is, have an optimum temperature for the enzymatic activity or a thermal denaturation temperature for the enzyme protein of 70° C. or higher), the hydrolysis reaction of the materials composed of lignocellulose containing cellulose by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of the material composed of lignocellulose containing cellulose, it becomes possible to conduct the hydrolysis reaction of the material in a high-temperature environment in which the hydrolysis temperature is from 70 to 90° C. With this high-temperature hydrolysis, the amount of enzymes and the time required for the hydrolysis can be reduced markedly, and the hydrolysis costs can be cut dramatically.

[Method for Producing Lignocellulose Degradation Product]

The method for producing a lignocellulose degradation product according to the present invention is a method for degrading a material composed of lignocellulose containing cellulose, for example, a material containing a compound with a β-glycosidic bond, to thereby obtain the degradation product thereof, with the thermostable β-glucosidase according to the present invention. More specifically, the lignocellulose degradation product (for example, a degradation product including monosaccharides such as glucose, xylose, and galactose) is generated by bringing a material composed of lignocellulose containing cellulose into contact with the thermostable β-glucosidase according to the present invention, the transformant according to the present invention, a thermostable β-glucosidase produced by the method for producing a thermostable β-glucosidase according to the present invention, or the glycoside hydrolase mixture according to the present invention.

The material composed of lignocellulose containing cellulose is not particularly limited as long as it contains cellulose. Specific examples of such materials include cellulosic biomass such as weeds and agricultural waste materials, or used paper or the like. The material containing cellulose is preferably subjected to a mechanical treatment such as crushing or shredding, a chemical treatment with acid or alkali or the like, or a treatment such as immersion or dissolution in an appropriate buffer, prior to being brought into contact with the thermostable β-glucosidase according to the present invention.

The reaction conditions for the hydrolysis reaction of the aforementioned material by the thermostable β-glucosidase according to the present invention may be any conditions under which the thermostable β-glucosidase exhibits β-glucosidase activity. For example, the reaction is preferably conducted at a temperature of 60 to 110° C. and a pH of 4.5 to 7.0, more preferably conducted at a temperature of 80 to 105° C. and a pH of 5.0 to 7.0, and still more preferably conducted at a temperature of 90 to 105° C. and a pH of 5.0 to 6.5. The reaction time for the hydrolysis reaction may be adjusted appropriately with due consideration of the type, the method of pretreatment, and the amount and the like of the aforementioned material that is supplied to the hydrolysis reaction. For example, the hydrolysis reaction may be performed for a reaction time of 10 minutes to 100 hours, but in the case of degradation of a cellulosic biomass, the hydrolysis reaction time is preferably from 1 to 100 hours.

In the hydrolysis reaction of the material composed of lignocellulose containing cellulose, it is also preferable to use at least one other type of glycoside hydrolase in addition to the thermostable β-glucosidase according to the present invention, with the enzymes used. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 85° C., preferably at least at a temperature of 70 to 90° C., more preferably at a temperature of 60 to 100° C., and still more preferably at a temperature of 60 to 110° C. Further, one aspect of the aforementioned method for producing a lignocellulose degradation product uses the thermostable β-glucosidase according to the present invention, the transformant according to the present invention, or a thermostable β-glucosidase produced by the method for producing a thermostable β-glucosidase according to the present invention, whereas another aspect of the method uses the aforementioned glycoside hydrolase mixture.

EXAMPLES

Next, the present invention is described in further detail based on a series of Examples, but the present invention is in no way limited by the following Examples.

Example 1

Cloning of Novel Thermostable β-Glucosidase from Hot Spring Soil

<1> DNA Extraction from Hot Spring Soil and Whole Genome Sequencing (WGS)

With the purpose of searching for genes of novel thermostable β-glucosidases which exhibit activity at a temperature of 60 to 110° C., soil DNA was collected from neutral to weakly alkaline hot springs, and nucleotide sequencing was conducted of the metagenomic DNA of the microbial flora contained in the soils.

The soil samples from neutral to weakly alkaline hot springs were obtained by collecting hot spring water containing soil, clay and biomat from five sampling points (metagenomic DNA samples N2, AR19, AR15, OJ1 and H1) at 3 locations in Japan having gushing high-temperature outdoor hot springs. These hot spring soil samples each had a temperature within a range from 58 to 78° C. and a pH within a range from 7.2 to 8 at the time of collection.

DNA was extracted from 10 g of each of the collected hot spring soil samples by using a DNA extraction kit (ISOIL Large for Beads ver.2, manufactured by NIPPON GENE Co., Ltd.). 5 µg of the extracted DNA was subjected to shotgun sequencing of the metagenomic DNA using the GS FLX Titanium 454 sequencer manufactured by Roche Diagnostics K.K. The remaining DNA was used for PCR cloning of the β-glucosidase gene.

Metagenomic DNA sequencing was carried out using the hot spring soil sample AR19 (hereinafter, may be referred to as an "AR19 metagenome"). By so doing, a whole genome sequence (WGS) data set was obtained with an average read length of 396 bp, a total read number of 2,766,332, and a total quantity of sequenced genomes of 1,106,243,280 bp.

<2> Assembly and Statistics of Hot Spring Metagenomic Data

The output from the Roche 454 (sff file) was rebasecalled with the PyroBayes (Quinlan et al., Nature Methods, 2008, vol. 5, p. 179-81), by which sequence files and quality value files in FASTA format were obtained. After clipping their ends to improve the quality, the obtained sequence reads were assembled with use of the assembly software, Newbler version 2.3 of 454 Life Sciences. The assembly was carried out under the settings of "minimum acceptable overlap match (mi)=0.9" and "option:-large (for large or complex genomes, speeds up assembly, but reduces accuracy)".

The total of the quality filter processed reads and 100 bp or longer assembled contigs was 104,096,316 bp, and this data set was used for the glycoside hydrolase gene analysis. Out of the total read number of 2,766,332 reads, 2,308,679 reads were assembled into 1,027 bp contigs in average (101,372 contigs in total). Of these, the maximum contig length was 187,970 bp.

<3> Prediction of Open Reading Frames (ORFs) of β-Glucosidase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: 2011/12/9) from the UniProt database (http://www.uniprot.org/), and a proteome local database of these glycoside hydrolase genes was constructed. Using the annotation software Orphelia (Hoff et al., Nucleic Acids Research, 2009, 37 (Web Server issue: W101-W105)), gene regions (=open reading frames) were predicted from the contig sequences obtained in section <2> above. In order to extract the glycoside hydrolase gene from the predicted ORFs, reference was made to the local database using BLASTP (blastall ver. 2.2.18). The optional conditions for BLASTP were set such that: "Filter query sequence=false", "Expectation value (E)<1e$^{-20}$" [hereafter, default values were set such that: "Cost to open a gap=−1", "Cost to extended gap=−1", "X dropoff value for gapped alignment=0", "Threshold for extending hits=0", and "Word size=default"], and the ORF sequences that hit any one of Glyco_hydro_3_C, Exo-1,4-beta glucosidase, Beta-glucosidase, Beta-d-glucosidase, B-glucosidase, Xylosidase, Glycoside hydrolase family 1, Glycoside hydrolase family 3, Glycoside hydrolase family 1, Glycoside hydrolase family 3, Beta-D-glucoside glucohydrolase, and Beta-galactosidase that were entered in the aforementioned local database were collected as β-glucosidase candidate sequences.

<4> Glycoside Hydrolase (GH) Family Classification of Genes

Functional classification of the β-glucosidase candidate sequences collected in section <3> above was performed with reference to the protein functional domain sequence database Pfam HMMs (Pfam version 23.0 and HMMER v2.3; Finn et al., Nucleic Acids Research Database, 2010, Issue 38, pp. D211-222). More specifically, the glycoside hydrolase (GH) family was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff<1e$^{-5}$; Database=Pfam_fs (models that can be used to find fragments of the represented domains in a sequence)).

The results of the GH family classification of 76 ORFs (38 full-length ORFs and 38 partial length ORFs, respectively) predicted as β-glucosidase candidate sequences are shown in Table 1. Those that covered 70% or more of the GH catalytic domain sequence were counted. As shown in Table 1, 10 full-length ORFs belonging to the GH family 1, 23 full-length ORFs belonging to the GH family 3, and 5 full-length ORFs belonging to the GH family 31 were obtained from the metagenome AR19, respectively. Primers were designed for all of the ORFs that were predicted as β-glucosidases, and these genes were cloned from the hot spring soil metagenomic DNA by PCR. As a result, a β-glucosidase candidate gene was isolated from the open reading frame AR19G-228 (SEQ ID NO: 3) predicted as a β-glucosidase candidate sequence which belonged to the GH family 1.

TABLE 1

| | GH family classification of β-glucosidase genes | | | |
|---|---|---|---|---|
| AR19 metagenome | GH1 | GH3 | GH31 | Total |
| Full-length ORFs | 10 | 23 | 5 | 38 |
| Partial length ORFs | 9 | 27 | 2 | 38 |
| Total number of ORFs | 19 | 50 | 7 | 76 |

<5> Open Reading Frame AR19G-228

The open reading frame AR19G-228 encoded a polypeptide (SEQ ID NO: 1) including 493 amino acid residues and was a full-length sequence (SEQ ID NO: 3), such that the polypeptide started from methionine which was an amino acid residue at position 1, and the 3' end of the nucleotide sequence encoding the polypeptide ended with a termination codon. Based on the sequence homology of the motif, it was presumed that the 470 amino acid residues from the phenylalanine (F) at position 2 through to the lysine (K) at position 471 encoded by the open reading frame AR19G-228 were the catalytic domain of glycoside hydrolase family 1. According to analysis using the signal sequence prediction software SignalP 4.1, no signal peptide was predicted within the amino acid sequence encoded by the open reading frame AR19G-228. This ORF was a novel sequence such that the amino acid sequence encoded by the ORF exhibited 68% amino acid sequence identity with the GH1 catalytic domain of the glycoside hydrolase family 1 of the bacterium *Thermotoga thermarum* DSM 5069 of the phylum Thermotogae. The sequence homology values were calculated using the ClustalW algorithm.

FIG. 1 shows an alignment of the amino acid sequence (SEQ ID NO: 1) of the open reading frame AR19G-228, and the amino acid sequence (SEQ ID NO: 8) of the glycoside hydrolase family 1 of *Thermotoga thermarum* DSM 5069 of the phylum Thermotogae. In FIG. 1, the amino acids shown in white on black are the amino acid residues identical to both amino acid sequences, the shaded amino acids are the amino acid residues similar to both amino acid sequences, and "-" indicates a gap in a sequence.

<6> Gene Cloning

Using a forward primer composed of the nucleotide sequence represented by SEQ ID NO: 7 (5'-CACCATGTTTCCAAAAGATTTTCTCTTCG-3': 4 nucleotides (CACC) were added to the 5'-end of the nucleotide sequence represented by SEQ ID NO: 5, wherein the CACC added to the 5' side is a sequence to enable insertion into a vector), and a reverse primer composed of the nucleotide sequence represented by SEQ ID NO: 6 (5'-TCAAACGTTCTGTTTCCAAATCTG-3'), PCR was performed using the hot spring soil DNA that had been amplified by the genome DNA amplification kit (GenomiPhi V2 DNA Amplification Kit, manufactured by GE Healthcare, Inc.) as a template. It should be noted that the nucleotide sequence represented by SEQ ID NO: 5 is homologous (identical) with the partial sequence composed of the nucleotides from positions 1 to 25 of the nucleotide sequence represented by SEQ ID NO: 3. Further, the nucleotide sequence represented by SEQ ID NO: 6 is complementary with the partial sequence composed of the nucleotides from positions 1,459 to 1,482 of the nucleotide sequence represented by SEQ ID NO: 3. The amplified PCR product was inserted into a pET101/D-TOPO vector of a Champion pET Directional TOPO Expression Kit (manufactured by Life Technologies Inc.), and transformed into a One Shot TOP10 strain. Positive clones were selected by colony PCR and cultured in an LB liquid medium containing 100 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a sequencer (3730 DNA Analyzer, manufactured by Life Technologies Corporation).

Three gene clones AR19G-228-1, AR19G-228-2, and AR19G-228-5 were obtained from the open reading frame AR19G-228 (SEQ ID NO: 3) by PCR cloning. The nucleotide sequence of the β-glucosidase candidate gene AR19G-228-1 (SEQ ID NO: 4) contained 1,482 bp like that of the open reading frame AR19G-228 (SEQ ID NO: 3), and was different from that of the predicted ORF by 2 nucleotides. In other words, the 416th nucleotide was A (adenine) in the open reading frame AR19G-228, whereas it was G (guanine) in the cloned AR19G-228-1 gene; and the 1,062th nucleotide was G (guanine) in the open reading frame AR19G-228, whereas it was A (adenine) in the cloned AR19G-228-1. Of these, differences in the nucleotides at one location also resulted in different amino acids, and the amino acid sequence of the open reading frame AR19G-228 (SEQ ID NO: 1) and the amino acid sequence of the β-glucosidase candidate gene AR19G-228-1 (SEQ ID NO: 3) were different by 1 amino acid residue. In other words, the amino acid residue at position 139 was lysine (K) in the open reading frame AR19G-228, whereas it was arginine (R) in the cloned AR19G-228-1 gene.

<7> Expression and Purification of β-Glucosidase Enzyme Protein

Following sequence confirmation, the plasmid having the target gene was introduced into *E. coli* for protein expression using the heat shock method. The BL21 Star (DE3) strain provided in the Champion pET Directional TOPO Expression Kit (manufactured by Life Technologies Inc.) was used as the competent cell for the transformation. Expression of the target protein was induced by inoculating the *E. coli* having the target gene into an LB medium containing 100 mg/L of ampicillin, culturing to about OD600=0.2 to 0.8, subsequently adding IPTG (isopropyl-β-D-(−)-thiogalactopyranoside), and performing additional culturing for 5 to 20 hours. Following completion of the culturing, the *E. coli* was collected by centrifugation, and an amount of 50 mM Tris-HCl buffer (pH 8.0) equivalent to 1/10 of the volume of the culture liquid was then added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant *E. coli* containing the target protein. This gene recombinant *E. coli* crude extract was filtered through a filter (pore size φ=0.45 mm, manufactured by EMD Millipore Corporation), and the resulting filtrate was used as a gene recombinant *E. coli* homogeneous supernatant.

The gene recombinant *E. coli* homogeneous supernatant was loaded onto an ion exchange column HiTrap Q HP (manufactured by GE Healthcare, Inc.) equilibrated with 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in 50 mM Tris-HCl buffer (pH 8.0) containing 1 M of NaCl. The fractions exhibiting β-glucosidase activity were pooled, and a centrifugal ultrafiltration membrane VIVASPIN 20 (manufactured by Sartorius stedim Biotech SA) was used to exchange the buffer to a 50 mM Tris-HCl buffer (pH 8.0) containing 750 mM of ammonium sulfate. The fractions with β-glucosidase activity following the buffer exchange were loaded onto a hydrophobic interaction separation column HiTrap Phenyl HP (manufactured by GE Healthcare, Inc.) equilibrated with the same solution, and the proteins were fractionated with a concentration gradient of 0 to 100% in 50 mM Tris-HCl buffer (pH 8.0). The fractions exhibiting β-glucosidase activity were pooled and then concentrated using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting β-glucosidase activity were pooled, subjected to a buffer exchange into 1 mM phosphoric acid buffer (pH 6.8) and concentrated by using the VIVASPIN 20, and then loaded onto a hydroxyapatite column CHT5-1 (manufactured by Bio-Rad Laboratories, Inc.) equilibrated with the same buffer, and the proteins were fractionated with a concentration gradient of 0 to 100% in a 400 mM phosphoric acid buffer (pH 6.8). The fractions exhibiting β-glucosidase activity were pooled, subjected to a buffer exchange into 50 mM Tris-HCl buffer (pH 8.0) and then concentrated, thus yielding a purified enzyme having a final concentration of about 1 mg/mL.

The gene recombinant *E. coli* homogenous supernatant and the purified enzyme (purified β-glucosidase enzyme protein) were checked by SDS-PAGE (SDS-polyacrylamide gel electrophoresis) analysis. The SDS-PAGE of the gene recombinant *E. coli* homogenous supernatant and the purified enzyme was performed using a Mini-PROTEAN TGX Stain-Free gel (manufactured by Bio-Rad Laboratories, Inc.). The supernatant or the purified enzyme were each mixed with Tris-SDS (WE treatment solution (manufactured by Cosmo Bio Co. Ltd.) at 1:1, and following treatment of the thus obtained samples at 100° C. for 10 minutes. Then, 10 mL of the gene recombinant *E. coli* homogenous supernatant and 2 μg of the purified enzyme were respectively electrophoresed. After the electrophoresis, the protein bands were visualized by CBB staining.

FIG. 2 shows the SDS-PAGE analysis results of the gene recombinant *E. coli* homogenous supernatant prepared from the transformed *E. coli* into which the AR19G-228-1 gene had been introduced, and the purified enzyme produced from the gene recombinant *E. coli* homogenous supernatant. The figure shows an electrophoretic pattern in which lane 1 represents a protein mass marker, lane 2 represents the gene recombinant *E. coli* homogenous supernatant, and lane 3 represents the purified enzyme. The results revealed a strong band in the gene recombinant *E. coli* homogenous supernatant (lane 2) near the mass of 57.1 kDa expected from the amino acid sequence (SEQ ID NO: 2), and a single band corresponding with this band (indicated by an arrow in the figure) was observed in the purified enzyme (lane 3).

<8> β-Glucosidase Activity Using PNPG as Substrate

The β-glucosidase activity using PNPG as a substrate of the enzyme protein (AR19G-228-1) encoded by the AR19G-228-1 gene was investigated. A solution prepared by dissolving PNPG (manufactured by Sigma-Aldrich Co. LLC.) in water and adjusting to a predetermined final concentration was used as the substrate solution. It should be noted that the PNPG substrate solutions used in the experiments described below all used the PNPG aqueous solution prepared by the above method. PNPG (manufactured by Sigma-Aldrich Co. LLC.) was used as the substrate for measuring the β-glucosidase activity. In the measurements, the purified enzyme obtained in section <7> above was diluted to a concentration of 0.0075 mg/mL with 0.05 M Tris-HCl buffer (pH 8.0) and used.

For the reaction at a temperature of 50 to 90° C., a Thermomixer (manufactured by the Eppendorf AG) was used, a sample tube with a volume of 1.5 mL was used as a reaction vessel, and the amount of reaction solution was set to 200 μL. The reaction solution was composed of 5 μL of diluted purified enzyme, 45 μL of purified water, 50 μL of 200 mM acetate buffer (pH 5.5), and 100 μL of 60 mM PNPG aqueous solution. For the reaction at a temperature of 95° C. to 110° C., the Reacti-Therm module (manufactured by Thermo Fisher Scientific, Inc.) was used, a glass vial with a volume of 1.5 mL was used as a reaction vessel, and the amount of reaction solution was set to 400 μL. The reaction solution was composed of 10 μL of diluted purified enzyme, 90 μL of purified water, 100 μL of 200 mM acetate buffer (pH 5.5), and 200 μL of 60 mM PNPG aqueous solution. It should be noted that the inside of the glass vial was coated with a 1.5% by mass BSA solution in advance in order to suppress the enzyme protein adsorption.

In all measurements, a mixed solution prepared by replacing the purified enzyme solution with 50 mM Tris-HCl buffer (pH 8.0) and then reacting the solution under the same conditions was used as a control. Further, the mixed solution containing the purified enzyme solution, the purified water and the buffer was preincubated at the reaction temperatures for 5 minutes, the substrate solution was then added, and the reaction was performed. Following completion of the reaction of 10 minutes, the reaction was stopped by adding the same volume of a 0.2 M $Na_2CO_3$ solution to the mixed solution with stirring, and the resulting mixture was then centrifuged to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then determining the amount of p-nitrophenol produced by the enzymatic hydrolysis by the difference from the control. The enzymatic activity for producing 1 μmol of p-nitrophenol per minute was defined as 1 U, and the value obtained by dividing this activity by the amount of protein was defined as the specific activity (U/mg). In addition, each measurement was performed for three independent experiments, and a mean value and a standard error were determined.

<9> Substrate Specificity of AR19G-228-1

The hydrolysis activity of the enzyme protein AR19G-228-1 against various cellulose substrates and hemicellulose substrates was investigated. In the measurements, the purified enzyme obtained in section <7> above was diluted to a concentration of 0.0075 mg/mL with 0.05 M Tris-HCl buffer (pH 8.0) and used. In addition, for the substrates, PNPG (manufactured by Sigma-Aldrich Co. LLC.), PNPGAL (manufactured by Sigma-Aldrich Co. LLC.), PNPX (manufactured by Sigma-Aldrich Co. LLC.), CMC (manufactured by Sigma-Aldrich Co. LLC.), PSA, Avicel powder and xylan (derived from beechwood, manufactured by Sigma-Aldrich Co. LLC.) were used.

The PSA was prepared by first dissolving Avicel powder (microcrystalline cellulose powder, manufactured by Merck & Co., Inc.) in a phosphoric acid solution, subsequently adding sterile distilled water to effect precipitation, and then performing washing until a pH of 5 or higher was reached. All the PSA used in the following experiments was prepared by this method.

More specifically, in the case of using PNPX, PNPG or PNPGAL as the substrate, the amount of p-nitrophenol produced by the enzymatic hydrolysis was determined and the specific activity (U/mg) was calculated in the same manner as in section <8> above, with the exception that the aqueous solution of 20 mM was used as the substrate solution to effect a reaction at 100° C.

In the case of using PSA, Avicel powder, CMC or xylan as the substrate, the reaction was effected in the same manner as in section <8> above, with the exception that the aqueous solution of 1% by mass was used as the substrate solution to effect a reaction at 100° C. Following completion of the reaction, an equal volume of a 3,5-dinitrosalicylic acid reagent (DNS solution) was added, and the resulting mixture was heated at 100° C. for 5 minutes, cooled down on ice for 5 minutes, and then centrifuged at 17,500 g for 5 minutes at room temperature to obtain a supernatant. The absorbance at 540 nm was measured using a spectrophotometer, the amount of reduced sugar in the supernatant was calculated using a calibration curve prepared with glucose (calibration curve prepared with xylose when xylan was used as a substrate), and the amount of reduced sugar produced by the enzymatic hydrolysis was calculated from the difference from the control. The enzymatic activity for producing 1 μmol of reduced sugar per minute was defined as 1 U, and the value obtained by dividing this activity by the amount of protein was defined as the specific activity (U/mg).

Figure 3:
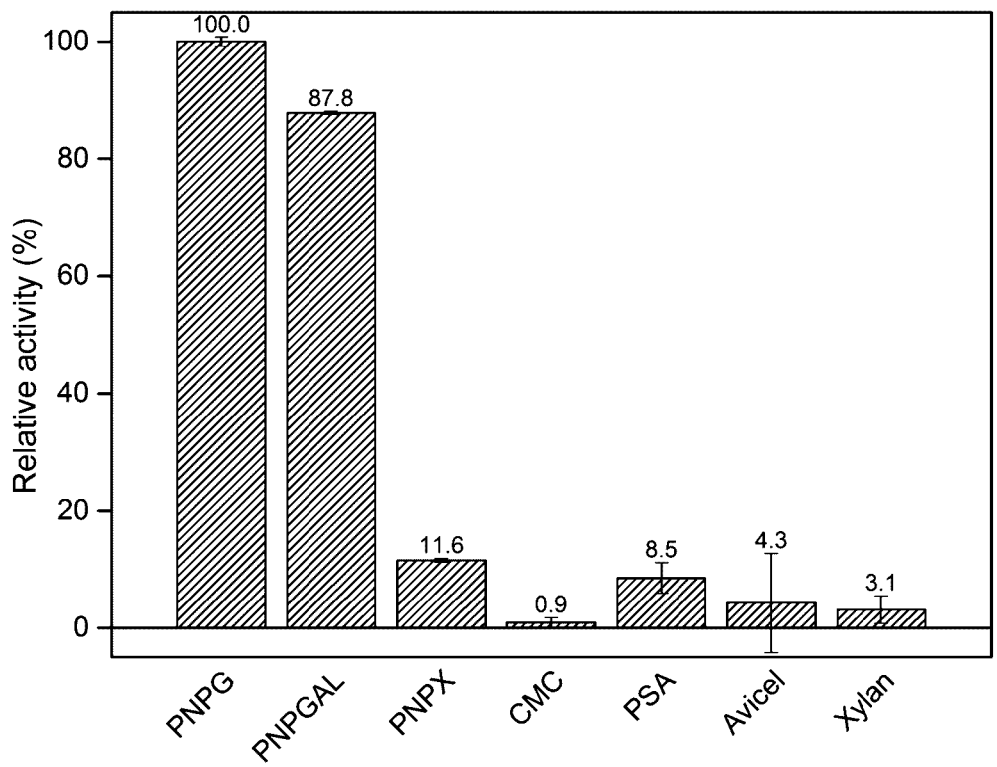
FIG. 3 is a diagram showing the results of measuring the hydrolytic activity (relative value calculated by taking the degradation activity for PNPG as 100%) of the AR19G-228-1 protein expressed in *E. coli* relative to various substrates in Example 1.

The measurement results are shown in FIG. 3. The enzymatic activity was shown as the relative value (Relative activity, %) calculated by taking the degradation activity against PNPG as 100%. The results revealed that AR19G-228-1 exhibited the highest hydrolytic activity against PNPG, and also exhibited a high level of hydrolytic activity against PNPGAL. In addition, AR19G-228-1 also exhibited weak hydrolytic activity against PNPX, and also exhibited hydrolytic activity against PSA, Avicel and xylan, although at a very low level. From these results, it was shown that AR19G-228-1 was β-glucosidase that also exhibited β-galactosidase activity, and also had a certain level of β-xylosidase activity.

<10> Kinetics of AR19G-228-1 β-Glucosidase

The maximum initial velocity ($V_{max}$) of PNPG hydrolysis by AR19G-228-1, the Michaelis constant ($K_m$) and the catalytic efficiency ($K_{cat}/K_m$) were investigated. Kinetics measurements were performed in the same manner as in section <8> above, with the exception that concentrations of PNPG aqueous solutions were set to 0.5 mM, 1 mM, 2 mM, 5 mM, 10 mM, 20 mM, 40 mM, 60 mM, 80 mM and 100 mM, and the reaction was effected at 100° C., thus calculating the PNPG hydrolysis activity (U/mg). The maximum initial velocity ($V_{max}$) and the Michaelis constant ($K_m$) were determined by fitting to a Michaelis-Menten model using the data analysis software Origin (manufactured by LightStone Corporation), and the catalytic efficiency ($K_{cat}/K_m$) was calculated from the obtained numerical values.

The results are shown in Table 2. The maximum initial velocity (Vmax), the Michaelis constant ($K_m$) and the catalytic efficiency ($K_{cat}/K_m$) for AR19G-228-1 were 430.3 U/mg, 4.5 mM, and 91.5/sec/mM, respectively.

TABLE 2

|  | $V_{max}$ (U/mg) | $K_m$ (mM) | $K_{cat}/K_m$ (/sec/mM) |
|---|---|---|---|
| AR19G-228-1 | 430.3 | 4.5 | 91.5 |

<11> Temperature and pH Dependencies of β-Glucosidase of AR19G-228-1

The temperature dependency of the PNPG hydrolytic activity of AR19G-228-1 was investigated. More specifically, measurement of the temperature dependency of the PNPG hydrolytic activity of AR19G-228-1 was conducted in the same manner as that described in section <8> above, with the exception of performing measurements at reaction temperatures of 50, 60, 70, 80, 90, 95, 100, 105 and 110° C., and for each temperature, the amount of p-nitrophenol produced by the enzymatic hydrolysis was determined, and the PNPG hydrolysis activity (U/mg) was calculated.

Figure 4:
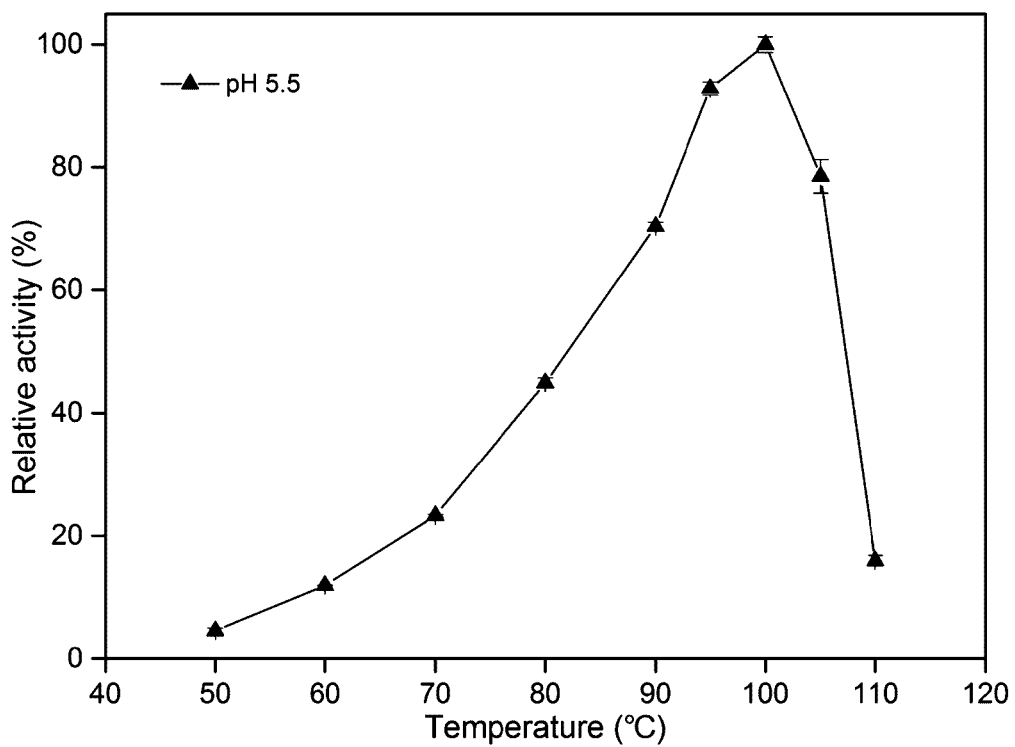
FIG. 4 is a diagram showing the results of measuring the PNPG hydrolytic activity (pH 5.5) (relative value calculated by taking the hydrolytic activity at 100° C. as 100%) of the AR19G-228-1 protein expressed in *E. coli* at various temperatures in Example 1.

The results are shown in FIG. 4. The enzymatic activity was shown as the relative value (Relative activity, %) calculated by taking the value at 100° C. that exhibited the highest degradation activity against PNPG as 100%. AR19G-228-1 exhibited PNPG hydrolysis activity in a temperature range from 50 to 110° C. (FIG. 4).

In the temperature range from 50 to 100° C., the PNPG hydrolysis activity also increased with an increase in the enzymatic reaction temperature, and the optimum temperature ($T_{opt}$) showing the highest activity was 100° C. When the enzymatic reaction temperature was set to 105° C. or higher, the PNPG hydrolytic activity decreased rapidly.

The pH dependency of the PNPG hydrolytic activity of AR19G-228-1 was investigated. More specifically, measurement of the pH dependency of the PNPG hydrolytic activity of AR19G-228-1 was conducted in the same manner as that described in section <8> above, with the exception of using 50 mL of McIlvaine's buffer (pH 3 to 8) and reacting at 100° C., and the amount of p-nitrophenol produced by the enzymatic hydrolysis was determined, and the PNPG hydrolysis activity (U/mg) was calculated for each of the pH values.

Figure 5:
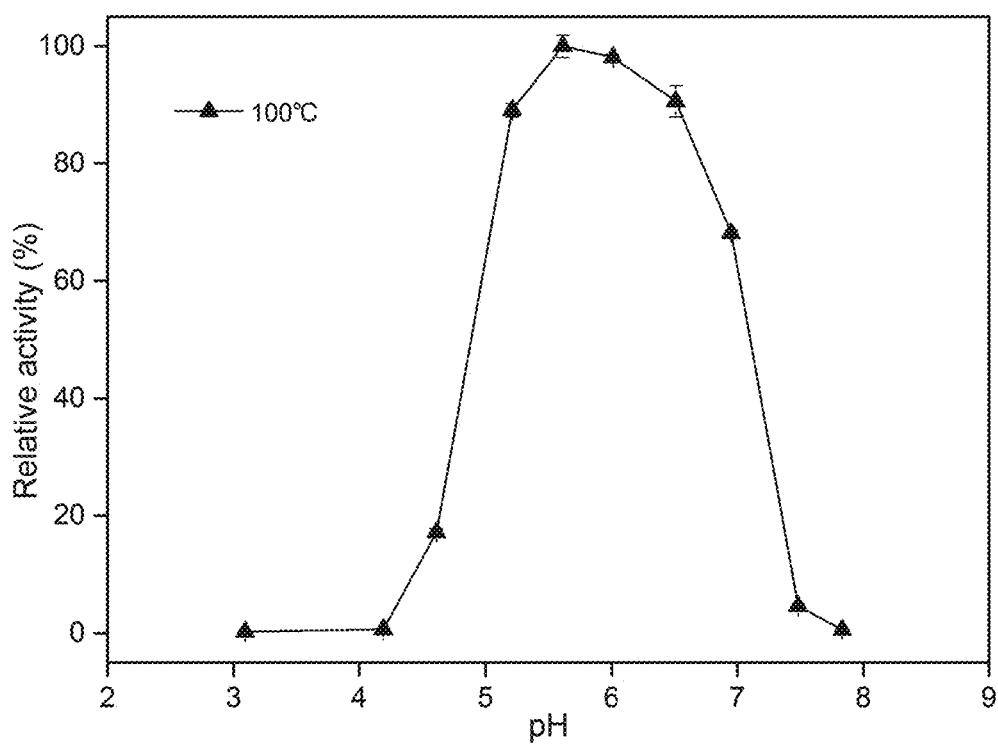
FIG. 5 is a diagram showing the results of measuring the PNPG hydrolytic activity (100° C.) (relative value calculated by taking the hydrolytic activity at a pH of 5.5 as 100%) of the AR19G-228-1 protein expressed in *E. coli* at various pH values in Example 1.

The measurement results are shown in FIG. 5. The enzymatic activity was shown as the relative value (Relative activity, %) calculated by taking the value at pH5.5 that exhibited the highest degradation activity against PNPG as 100%. For the pH, the actual measurement value obtained for the mixed solution containing the substrate, the buffer and the enzyme was plotted. AR19G-228-1 exhibited PNPG hydrolysis activity in a pH range from 4.5 to 7.5. The optimum pH was a pH of 5.61 (actual measurement value obtained for the mixed solution containing the substrate, the buffer, and the enzyme).

<12> Thermal Stability Measurement of β-Glucosidase

The thermal stability of the PNPG hydrolysis activity by AR19G-228-1 was investigated. In the measurements, the purified enzyme obtained in section <7> above was diluted to a concentration of 0.0075 mg/mL with 0.05 M Tris-HCl buffer (pH 8.0) and used.

More specifically, measurements were performed by holding (preincubating) the mixed solution composed of 10 μL of diluted purified enzyme, 90 μL of purified water and 100 μL of 200 mM acetate buffer (pH 5.5) at temperatures of 90° C., 95° C., 100° C. and 105° C. for 0, 30, 60 or 120 minutes, and then measuring the PNPG hydrolytic activity in the same manner as in section <8> above at 90° C. It should be noted that for the measurement of thermal stability, the Reacti-Therm module (manufactured by Thermo Fisher Scientific Inc.) was used, and a glass vial with a volume of 1.5 mL was used as a reaction vessel.

Figure 6:
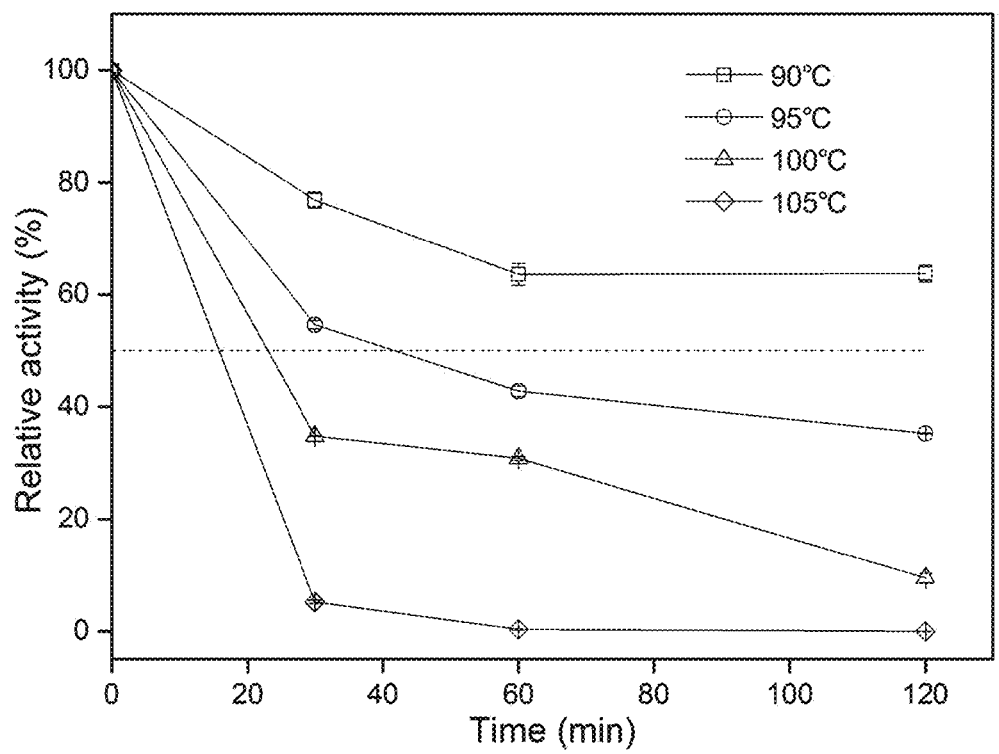
FIG. 6 is a diagram showing the results of measuring the thermal stability (pH 5.5) (relative value calculated by taking the activity of an untreated sample (at a temperature holding time of 0 minutes) as 100%) of the PNPG hydrolytic activity of the AR19G-228-1 protein expressed in *E. coli* in Example 1.

The measurement results are shown in FIG. 6. The enzymatic activity was shown as the relative value (Relative activity, %) assuming that the activity of the untreated group (at a holding time of 0 minutes) was 100%. The holding time at which the enzymatic activity was reduced to 50% of the activity of the untreated group was defined as the half-life $T_{half}$. When the holding temperature was 90° C., AR19G-228-1 retained the PNPG hydrolytic activity of at least 60% even after the lapse of a holding time of 120 minutes. Half-lives $T_{half}$ at temperatures of 95° C., 100° C. and 105° C. were about 40 minutes, about 25 minutes, and about 15 minutes, respectively.

<13> Measurement of β-Glucosidase Activity in the Presence of Glucose

The PNPG hydrolysis activity by AR19G-228-1 in the presence of glucose was investigated.

In the measurements, the purified enzyme obtained in section <7> above was diluted to a concentration of 0.0075 mg/mL with 0.05 M Tris-HCl buffer (pH 8.0) and used.

More specifically, the reaction solution was prepared by mixing 10 μL of diluted purified enzyme, 50 μL of 400 mM acetate buffer (pH 5.5), 100 μL of PNPG aqueous solution, and 240 μL of glucose aqueous solution. The PNPG aqueous solution was adjusted so that the final concentration was 5, 15 or 30 mM, and the glucose aqueous solution was adjusted so that the final concentration was 0.6, 1.2, 1.8, 2.4 or 3 M. The mixed solution of the purified enzyme and the buffer was preincubated for 5 minutes at 100° C., and the PNPG aqueous solution and the glucose aqueous solution were then added thereto to initiate the reaction. After reaction of 10 minutes at 100° C., the PNPG hydrolytic activity was determined in the same manner as in section <8> above.

Figure 7:
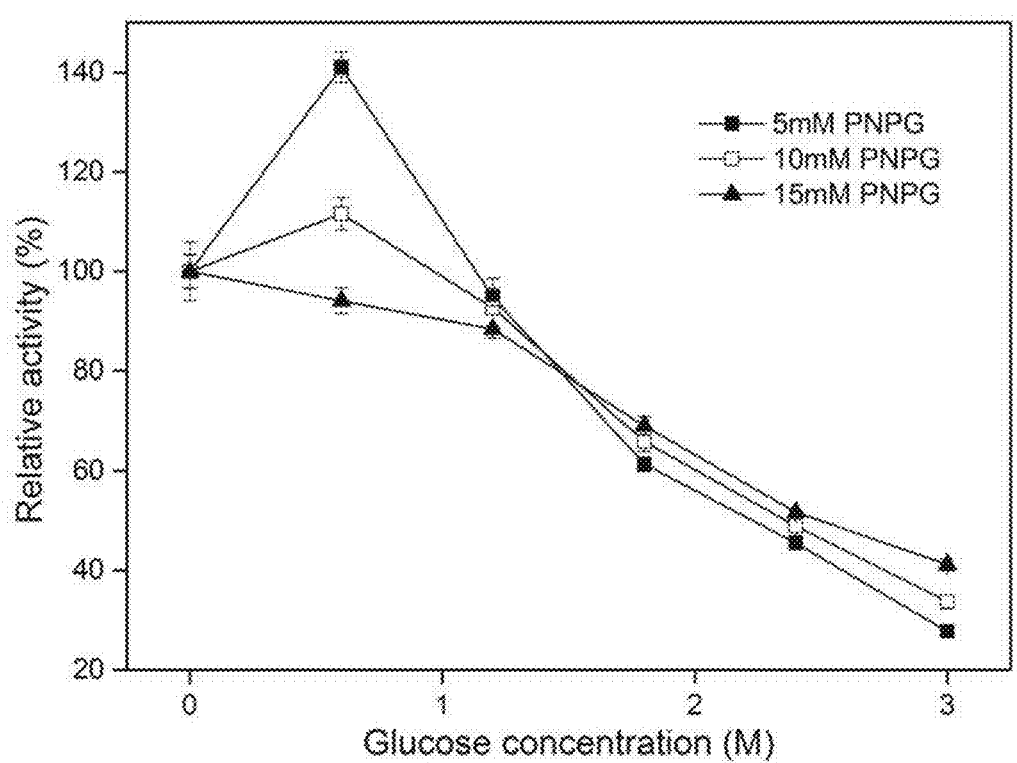
FIG. 7 is a diagram showing the results of measuring the PNPG hydrolytic activity (pH 5.5) (relative value calculated by taking the activity in a case where the glucose concentration is 0 M as 100%) of the AR19G-228-1 protein expressed in *E. coli* in the presence of glucose in Example 1.

The results are shown in FIG. 7. The enzymatic activity was shown as the relative value (Relative activity, %) assuming that the activity in the absence of glucose (that is, at a glucose concentration of 0 M) at the respective PNPG concentrations was 100%. Regardless of PNPG concentrations, AR19G-228-1 retained at least 80% of the activity in the absence of glucose even at a glucose concentration of 1.2 M, and still retained around 50% of the activity even at a glucose concentration of 2.4 M. To date, there have been no reports of β-glucosidase activity exhibiting the PNPG hydrolytic activity in the presence of glucose in such high concentrations. For example, in Non-Patent Document 3 or 4, the glucose concentrations at which the activity reaches 50% are 1.4 M and 1.36 M, respectively.

[Sequence Listings]

What is claimed is:

1. A thermostable β-glucosidase comprising a polypeptide consisting of the amino acid sequence of SEQ ID NO:1 or 2 and at least one domain selected from the group consisting of a cellulose-binding module, a linker domain, a signal peptide and a tag.

2. A glycoside hydrolase mixture, comprising the thermostable β-glucosidase according to claim 1 and at least one other glycoside hydrolase.

3. A method for producing a lignocellulose degradation product, the method comprising generating a lignocellulose degradation product by bringing a material comprising lignocellulose including cellulose into contact with the thermostable β-glucosidase according to claim 1.

4. A method for producing a lignocellulose degradation product, the method comprising generating a lignocellulose degradation product by bringing a material comprising lignocellulose including cellulose into contact with the glycoside hydrolase mixture according to claim 2.

* * * * *

```
SEQUENCE LISTING

<160> NUMBER OF SEQ ID NOS: 8

<210> SEQ ID NO 1
<211> LENGTH: 493
<212> TYPE: PRT
<213> ORGANISM: Unknown
<220> FEATURE:
<223> OTHER INFORMATION: Open reading frame AR19G-228

<400> SEQUENCE: 1

Met Phe Pro Lys Asp Phe Leu Phe Gly Ala Ser Met Ser Gly Phe Gln
```

```
1               5                   10                  15
Val Glu Met Gly Tyr Ala Lys Gly Asp Ile Asp Ala Asn Thr Asp Trp
                20                  25                  30
Phe Val Trp Val Arg Glu Pro Glu Asn Leu Ile Asn Ala Val Val Ser
                35                  40                  45
Gly His Leu Pro Glu Tyr Gly Val Gly Tyr Trp Tyr Asn Phe Pro Thr
                50                  55                  60
Ile His Lys Leu Ala Ser Asp Phe Gly Met Asn Val Leu Arg Thr Asn
65                  70                  75                  80
Ile Glu Trp Ser Arg Ile Phe Pro Thr Pro Thr Phe Asp Val Lys Val
                85                  90                  95
Glu Ile Glu Arg Thr Glu Ser Gly Ile Val Ser Val Gln Ile Asp Glu
                100                 105                 110
Arg Ala Leu Lys Gln Leu Asp Glu Leu Ala Asn Arg Glu Ala Val Glu
                115                 120                 125
His Tyr Arg Glu Ile Phe Ser Asp Met Arg Lys Arg Gly Leu Lys Val
                130                 135                 140
Phe Val Asn Leu Ile His Phe Thr Leu Pro Ile Trp Leu His Asp Pro
145                 150                 155                 160
Ile Ala Val His Arg Arg Gln Pro Thr Asp Lys Leu Gly Trp Ala Ser
                165                 170                 175
Glu Asn Thr Ile Val Glu Phe Thr Lys Phe Ala Ala Tyr Val Val Trp
                180                 185                 190
Lys Phe Asp Asp Leu Ile Asp Met Tyr Ser Thr Phe Asn Glu Pro Asn
                195                 200                 205
Val Val Ser Gln Met Gly Tyr Val Met Ser Val Ser Gly Phe Pro Pro
                210                 215                 220
Gly Ile Phe Asp Thr Glu Lys Phe Phe Asn Ser Phe Val Asn Gln Ile
225                 230                 235                 240
Val Ala His Ala Arg Ala Tyr Asp Ala Met Lys Lys Leu Thr Asp Lys
                245                 250                 255
Pro Ile Gly Leu Ile Tyr Ser Ala Ser Val Tyr Glu Ser Thr Asp Gly
                260                 265                 270
Asp Ala Glu Leu Glu Glu Ser Val Thr His Phe Met Asn Phe Phe Phe
                275                 280                 285
Leu Asp Ala Leu His Ser Gly Thr Met Phe Phe Arg Thr Arg Glu Asp
                290                 295                 300
Leu Ala Gly Arg Leu Asp Phe Ile Gly Leu Asn Tyr Tyr Thr Arg Thr
305                 310                 315                 320
Val Ile Gln Arg Ser Leu Gln Glu Leu Ser Phe Gly Pro Val Ser Met
                325                 330                 335
Ser Trp Ser Ile Val Pro Gly Tyr Gly Tyr Ala Cys Gln Pro Ala Gly
                340                 345                 350
Phe Ser Lys Asp Gly Arg Pro Val Ser Asp Phe Gly Trp Glu Thr Tyr
                355                 360                 365
Pro Glu Gly Leu Leu Lys Leu Leu Arg Ala Phe Asp Glu Arg Tyr Ala
                370                 375                 380
Leu Pro Ile Tyr Val Thr Glu Asn Gly Val Ala Asp Ala Arg Asp Trp
385                 390                 395                 400
Leu Arg Pro Tyr His Leu Val Ala His Met Tyr Ala Val Glu Lys Ala
                405                 410                 415
Ile Glu Glu Gly Leu Asn Val Lys Gly Tyr Leu His Trp Ser Ile Val
                420                 425                 430
```

```
Asp Asn Tyr Glu Trp Ala Lys Gly Tyr His Met Arg Phe Gly Met Ala
            435                 440                 445

Glu Thr Asn Tyr Gln Thr Lys Ser Tyr Thr Pro Arg Pro Ser Met Tyr
450                 455                 460

Ile Phe Arg Glu Ile Val Lys Asn Leu Ser Thr Glu Lys Phe Arg Ser
465                 470                 475                 480

Tyr Leu Gln Ser Pro Tyr Gln Ile Trp Lys Gln Asn Val
            485                 490

<210> SEQ ID NO 2
<211> LENGTH: 493
<212> TYPE: PRT
<213> ORGANISM: Unknown
<220> FEATURE:
<223> OTHER INFORMATION: AR19G-228-1

<400> SEQUENCE: 2

Met Phe Pro Lys Asp Phe Leu Phe Gly Ala Ser Met Ser Gly Phe Gln
1               5                   10                  15

Val Glu Met Gly Tyr Ala Lys Gly Asp Ile Asp Ala Asn Thr Asp Trp
            20                  25                  30

Phe Val Trp Val Arg Glu Pro Glu Asn Leu Ile Asn Ala Val Val Ser
        35                  40                  45

Gly His Leu Pro Glu Tyr Gly Val Gly Tyr Trp Tyr Asn Phe Pro Thr
    50                  55                  60

Ile His Lys Leu Ala Ser Asp Phe Gly Met Asn Val Leu Arg Thr Asn
65                  70                  75                  80

Ile Glu Trp Ser Arg Ile Phe Pro Thr Pro Thr Phe Asp Val Lys Val
                85                  90                  95

Glu Ile Glu Arg Thr Glu Ser Gly Ile Val Ser Val Gln Ile Asp Glu
            100                 105                 110

Arg Ala Leu Lys Gln Leu Asp Glu Leu Ala Asn Arg Glu Ala Val Glu
        115                 120                 125

His Tyr Arg Glu Ile Phe Ser Asp Met Arg Arg Gly Leu Lys Val
    130                 135                 140

Phe Val Asn Leu Ile His Phe Thr Leu Pro Ile Trp Leu His Asp Pro
145                 150                 155                 160

Ile Ala Val His Arg Arg Gln Pro Thr Asp Lys Leu Gly Trp Ala Ser
                165                 170                 175

Glu Asn Thr Ile Val Glu Phe Thr Lys Phe Ala Ala Tyr Val Val Trp
            180                 185                 190

Lys Phe Asp Asp Leu Ile Asp Met Tyr Ser Thr Phe Asn Glu Pro Asn
        195                 200                 205

Val Val Ser Gln Met Gly Tyr Val Met Ser Val Ser Gly Phe Pro Pro
    210                 215                 220

Gly Ile Phe Asp Thr Glu Lys Phe Phe Asn Ser Phe Val Asn Gln Ile
225                 230                 235                 240

Val Ala His Ala Arg Ala Tyr Asp Ala Met Lys Lys Leu Thr Asp Lys
                245                 250                 255

Pro Ile Gly Leu Ile Tyr Ser Ala Ser Val Tyr Glu Ser Thr Asp Gly
            260                 265                 270

Asp Ala Glu Leu Glu Glu Ser Val Thr His Phe Met Asn Phe Phe Phe
        275                 280                 285

Leu Asp Ala Leu His Ser Gly Thr Met Phe Phe Arg Thr Arg Glu Asp
    290                 295                 300
```

Leu Ala Gly Arg Leu Asp Phe Ile Gly Leu Asn Tyr Tyr Thr Arg Thr
305                 310                 315                 320

Val Ile Gln Arg Ser Leu Gln Glu Leu Ser Phe Gly Pro Val Ser Met
            325                 330                 335

Ser Trp Ser Ile Val Pro Gly Tyr Gly Tyr Ala Cys Gln Pro Ala Gly
        340                 345                 350

Phe Ser Lys Asp Gly Arg Pro Val Ser Asp Phe Gly Trp Glu Thr Tyr
    355                 360                 365

Pro Glu Gly Leu Leu Lys Leu Leu Arg Ala Phe Asp Glu Arg Tyr Ala
370                 375                 380

Leu Pro Ile Tyr Val Thr Glu Asn Gly Val Ala Asp Ala Arg Asp Trp
385                 390                 395                 400

Leu Arg Pro Tyr His Leu Val Ala His Met Tyr Ala Val Glu Lys Ala
                405                 410                 415

Ile Glu Glu Gly Leu Asn Val Lys Gly Tyr Leu His Trp Ser Ile Val
            420                 425                 430

Asp Asn Tyr Glu Trp Ala Lys Gly Tyr His Met Arg Phe Gly Met Ala
        435                 440                 445

Glu Thr Asn Tyr Gln Thr Lys Ser Tyr Thr Pro Arg Pro Ser Met Tyr
    450                 455                 460

Ile Phe Arg Glu Ile Val Lys Asn Leu Ser Thr Glu Lys Phe Arg Ser
465                 470                 475                 480

Tyr Leu Gln Ser Pro Tyr Gln Ile Trp Lys Gln Asn Val
                485                 490

<210> SEQ ID NO 3
<211> LENGTH: 1482
<212> TYPE: DNA
<213> ORGANISM: Unknown
<220> FEATURE:
<223> OTHER INFORMATION: Open reading frame AR19G-228

<400> SEQUENCE: 3
atgtttccaa aagatttct cttcggagcg tcgatgtcag gttttcaggt cgagatgggt      60
tacgcgaagg gtgatatcga tgccaacacg gactggttcg tgtgggtgag ggaacctgaa     120
aatctcatta cgctgtcgt gagcggacat ctgccggagt acggtgtggg ttactggtac     180
aatttcccta cgatccacaa gctcgccagc gatttcggaa tgaacgttct tcgaacgaac    240
atcgagtggt ctcgcatctt tcccaccccc acgttcgatg tgaaagtcga aatagaacga    300
accgaatctg gaattgtatc ggtacagatc gacgaacggg ccctcaagca actggacgag    360
cttgccaaca gagaagcagt ggagcattat cgtgagatct tctcagacat gagaaagagg    420
ggcttgaaag ttttcgtcaa tctcatccat ttcacccctc ccatttggtt gcacgatccg    480
atcgccgtgc acagaagaca accgaccgac aaactcggat gggcaagtga aacactatc    540 gtcgaattta cgaaatttgc cgcctacgtc gtctggaagt cgacgatct aatcgacatg    600 tacagcacct ttaacgagcc gaacgttgtg agtcagatgg gttacgtgat gagtgtgtct    660
ggttttcctc ctggaatctt cgacacagaa aagttttca acagcttcgt gaaccagatc    720
gtcgcgcacg cgcgtgccta cgatgcaatg aaaaaactga cagacaagcc cattggcttg    780
atctactcgg catcggtgta cgaatcgaca gatggcgatg ctgaactcga agagagcgtg    840
acccatttca tgaacttctt cttcctcgat gccctgcaca gcgggaccat gttcttccgg    900
acgagggaag atttggcggg cagactcgac ttcatcggac taaactatta cacacgtacc    960

| | |
|---|---|
| gtgatccaaa gatctttgca agagctgagc ttcggtcctg tgagcatgag ttggtccatc | 1020 |
| gttccgggct acggttacgc gtgccagcca gctggtttct cgaaagatgg gaggcccgtg | 1080 |
| agtgacttcg gttgggaaac ttatcctgag ggtctgctga aacttttgcg tgccttcgac | 1140 |
| gagcgttacg ctctgcccat atatgtgact gagaacggag tggccgacgc gcgagactgg | 1200 |
| ctcaggcctt accaccttgt ggcacacatg tacgccgtcg aaaaggcgat tgaggaaggt | 1260 |
| ttgaacgtca aagggtatct gcactggtcg atcgtcgaca actacgaatg ggcgaagggt | 1320 |
| taccatatga ggttcggcat ggccgagacg aactaccaga cgaaatcgta caccccgaga | 1380 |
| ccttcgatgt acatcttcag agagatcgtg aaaaatttgt ccacggaaaa gttcagaagc | 1440 |
| tatctgcagt caccgtacca gatttggaaa cagaacgttt ga | 1482 |

<210> SEQ ID NO 4
<211> LENGTH: 1482
<212> TYPE: DNA
<213> ORGANISM: Unknown
<220> FEATURE:
<223> OTHER INFORMATION: AR19G-228-1

<400> SEQUENCE: 4

| | |
|---|---|
| atgtttccaa aagatttct cttcggagcg tcgatgtcag gttttcaggt cgagatgggt | 60 |
| tacgcgaagg gtgatatcga tgccaacacg gactggttcg tgtgggtgag ggaacctgaa | 120 |
| aatctcatta cgctgtcgt gagcggacat ctgccggagt acggtgtggg ttactggtac | 180 |
| aatttcccta cgatccacaa gctcgccagc gatttcggaa tgaacgttct tcgaacgaac | 240 |
| atcgagtggt ctcgcatctt tcccaccccc acgttcgatg tgaaagtcga aatagaacga | 300 |
| accgaatctg gaattgtatc ggtacagatc gacgaacggg ccctcaagca actggacgag | 360 |
| cttgccaaca gagaagcagt ggagcattat cgtgagatct tctcagacat gagaaggagg | 420 |
| ggcttgaaag ttttcgtcaa tctcatccat ttcaccctcc ccatttggtt gcacgatccg | 480 |
| atcgccgtgc acagaagaca accgaccgac aaactcggat gggcaagtga aaacactatc | 540 |
| gtcgaattta cgaaatttgc cgcctacgtc gtctggaagt cgacgatctc aatcgacatg | 600 |
| tacagcaccc ttaacgagcc gaacgttgtg agtcagatgg ttacgtgat gagtgtgtct | 660 |
| ggttttcctc ctggaatctt cgacacagaa aagttttca acagcttcgt gaaccagatc | 720 |
| gtcgcgcacg cgcgtgccta cgatgcaatg aaaaaactga cagacaagcc cattggcttg | 780 |
| atctactcgg catcggtgta cgaatcgaca gatggcgatg ctgaactcga agagagcgtg | 840 |
| acccatttca tgaacttctt cttcctcgat gccctgcaca gcgggaccat gttcttccgg | 900 |
| acgagggaag atttggcggg cagactcgac ttcatcggac taaactatta cacacgtacc | 960 |
| gtgatccaaa gatctttgca agagctgagc ttcggtcctg tgagcatgag ttggtccatc | 1020 |
| gttccgggct acggttacgc gtgccagcca gctggtttct caaaagatgg gaggcccgtg | 1080 |
| agtgacttcg gttgggaaac ttatcctgag ggtctgctga aacttttgcg tgccttcgac | 1140 |
| gagcgttacg ctctgcccat atatgtgact gagaacggag tggccgacgc gcgagactgg | 1200 |
| ctcaggcctt accaccttgt ggcacacatg tacgccgtcg aaaaggcgat tgaggaaggt | 1260 |
| ttgaacgtca aagggtatct gcactggtcg atcgtcgaca actacgaatg ggcgaagggt | 1320 |
| taccatatga ggttcggcat ggccgagacg aactaccaga cgaaatcgta caccccgaga | 1380 |
| ccttcgatgt acatcttcag agagatcgtg aaaaatttgt ccacggaaaa gttcagaagc | 1440 |
| tatctgcagt caccgtacca gatttggaaa cagaacgttt ga | 1482 |

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer.

<400> SEQUENCE: 5
atgtttccaa aagatttct cttcg                                          25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer.

<400> SEQUENCE: 6
tcaaacgttc tgtttccaaa tctg                                          24

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer.

<400> SEQUENCE: 7
caccatgttt ccaaaagatt ttctcttcg                                     29

<210> SEQ ID NO 8
<211> LENGTH: 489
<212> TYPE: PRT
<213> ORGANISM: Thermotoga thermarum DSM 5069
<220> FEATURE:
<223> OTHER INFORMATION: Glycoside hydrolase family 1

<400> SEQUENCE: 8
```

Met Phe Pro Lys Asp Phe Leu Phe Gly Ala Ser Met Ala Gly Phe Gln
1               5                   10                  15

Val Glu Met Gly Tyr Gly Lys Asp Asp Val Asp Pro Asn Thr Asp Trp
            20                  25                  30

Phe Val Trp Val Arg Glu Pro Glu Asn Leu Phe Thr Gly Thr Val Ser
        35                  40                  45

Gly His Leu Pro Glu Tyr Gly Val Gly Tyr Trp Lys Asn Tyr Ala Asn
    50                  55                  60

Leu His Gln Leu Ala Val Asp Phe Gly Met Asn Cys Leu Arg Val Asn
65                  70                  75                  80

Val Glu Trp Ser Arg Ile Phe Pro Lys Pro Thr Phe Asp Val Pro Val
                85                  90                  95

His Val Val Ser Glu Asn Gly Ile Arg Glu Val Lys Ile Asp Lys Thr
            100                 105                 110

Ser Leu Glu Lys Leu Asp Glu Ile Ala Asn Lys Ser Ala Val Glu His
        115                 120                 125

Tyr Arg Glu Ile Phe Lys Asp Met Lys Ser Arg Gly Leu Arg Leu Ile
    130                 135                 140

Leu Asn Leu Ala His Phe Thr Leu Pro Ile Trp Ile His Asp Pro Met
145                 150                 155                 160

Ala Val His Arg Gly Ile Pro Thr Glu Lys Thr Gly Trp Val Asn Glu
                165                 170                 175

Lys Thr Val Val Glu Phe Ala Lys Phe Ala Ala Tyr Val Ala Trp Lys

```
              180             185             190
Phe Asp Asp Leu Val Asp Met Tyr Thr Thr Met Asn Glu Pro Asn Val
        195             200             205

Val Ser Gln Met Gly Tyr Ile Met Thr Arg Gly Gly Phe Pro Pro Ser
        210             215             220

Tyr Phe Ser Pro Glu Met Tyr Leu Lys Ser Leu Phe Asn Gln Ala Gln
225             230             235             240

Ala His Ala Arg Ala Tyr Asp Ala Ile Lys Phe Leu Thr Glu Lys Pro
        245             250             255

Val Gly Ile Ile Tyr Ala Ser Ser Ile Tyr Glu Thr Leu Asn Gly Asp
        260             265             270

Lys Glu Ile Glu Glu Asn Ala Met Tyr Met Met Asn Tyr Met Phe Leu
        275             280             285

Asp Ser Ile Ile Asn Gly Ser Leu Leu Phe Gln Asp Arg Pro Asp Met
        290             295             300

Arg Glu Lys Val Asp Phe Leu Gly Val Asn Tyr Tyr Thr Arg Thr Val
305             310             315             320

Ile Glu Arg Ile Glu Pro Met Asn Phe Gly Gln Ile Ala Leu Asn Trp
                325             330             335

Lys Ile Leu Glu Gly Tyr Gly Tyr Ala Cys Pro Pro Gly Gly Phe Ser
                340             345             350

Lys Asp Phe Arg Pro Val Ser Asp Phe Gly Trp Glu Thr Tyr Pro Glu
        355             360             365

Gly Leu Leu Lys Leu Leu Arg Ala Phe Tyr Glu Arg Tyr Lys Leu Pro
        370             375             380

Leu Met Val Thr Glu Asn Gly Val Ala Asp Cys Arg Asp Trp Leu Arg
385             390             395             400

Pro Tyr His Leu Val Gly His Leu Tyr Ala Val Glu Lys Ala Ile Glu
                405             410             415

Asp Gly Ile Asp Val Arg Gly Tyr Leu His Trp Ser Ile Val Asp Asn
                420             425             430

Tyr Glu Trp Ala Arg Gly Tyr Thr Met Arg Phe Gly Leu Ala Glu Thr
        435             440             445

Asp Tyr Glu Thr Lys Gln Leu Thr Pro Arg Pro Ser Met Tyr Ile Phe
        450             455             460

Arg Glu Ile Val Lys Glu Gly Thr Thr Ala Arg Phe His Asn Tyr Leu
465             470             475             480

Lys Ser Pro Tyr Glu Ile Trp Arg Met
                485
```